United States Patent
Sullivan et al.

(10) Patent No.: US 10,519,257 B2
(45) Date of Patent: Dec. 31, 2019

(54) COMPOSITIONS CONTAINING 1,1-DI-CARBONYL-SUBSTITUTED ALKENE COMPOUNDS FOR PREPARING POLYMERS HAVING ENHANCED GLASS TRANSITION TEMPERATURES

(71) Applicant: SIRRUS, INC., Loveland, OH (US)

(72) Inventors: Jeffrey M. Sullivan, Goshen, OH (US); Aniruddha Palsule, Cincinnati, OH (US); Alexander R. Holzer, Cincinnati, OH (US); Kshitij K. Parab, Loveland, OH (US); Ami Doshi, Loveland, OH (US)

(73) Assignee: Sirrus, Inc., Loveland, OH (US)

( * ) Notice: Subject to any disclaimer, the term of this patent is extended or adjusted under 35 U.S.C. 154(b) by 0 days.

(21) Appl. No.: 15/857,808

(22) Filed: Dec. 29, 2017

(65) Prior Publication Data

US 2019/0202947 A1 Jul. 4, 2019

Related U.S. Application Data

(63) Continuation of application No. 15/783,181, filed on Oct. 13, 2017, now Pat. No. 9,890,227, which is a continuation of application No. 15/088,340, filed on Apr. 1, 2016, now Pat. No. 9,790,295, which is a continuation of application No. 14/859,992, filed on Sep. 21, 2015, now Pat. No. 9,315,597, which is a continuation-in-part of application No. PCT/US2015/048846, filed on Sep. 8, 5015, and a continuation-in-part of application No. 14/810,741, filed on Jul. 28, 2015, now Pat. No. 9,279,022, said application No. 14/859,992 is a continuation-in-part of application No. 14/789,178, filed on Jul. 1, 2015, now Pat. No. 9,249,265, said application No. 14/859,992 is a continuation-in-part of application No. 14/814,961, filed on Jul. 31, 2015, now Pat. No. 9,416,091.

(60) Provisional application No. 62/219,194, filed on Sep. 16, 2015, provisional application No. 62/047,283, filed on Sep. 8, 2014, provisional application No. 62/215,360, filed on Sep. 8, 2015, provisional application No. 62/186,479, filed on Jun. 30, 2015, provisional application No. 62/047,328, filed on Sep. 8, 2014, provisional application No. 62/182,076, filed on Jun. 19, 2015, provisional application No. 62/111,919, filed on Feb. 4, 2015, provisional application No. 62/198,844, filed on Jul. 30, 2015.

(51) Int. Cl.
*C08F 22/10* (2006.01)
*C07C 69/50* (2006.01)
*C08F 222/14* (2006.01)
*C09J 135/02* (2006.01)
*C08F 2/06* (2006.01)
*C07C 69/593* (2006.01)

(52) U.S. Cl.
CPC ............ *C08F 22/10* (2013.01); *C07C 69/593* (2013.01); *C08F 2/06* (2013.01); *C08F 222/14* (2013.01); *C09J 135/02* (2013.01)

(58) Field of Classification Search
CPC .......... C08F 22/10; C08F 222/14; C08F 2/06; C07C 69/593; C09J 135/02
USPC ...................................................... 526/321
See application file for complete search history.

(56) References Cited

U.S. PATENT DOCUMENTS

| | | |
|---|---|---|
| 2,212,506 A | 8/1940 | Bachman |
| 2,245,567 A | 6/1941 | Brant et al. |
| 2,403,791 A | 7/1941 | D'Aiello |
| 2,277,479 A | 3/1942 | D'Aiello |
| 2,313,501 A | 3/1943 | Bachman et al. |
| 2,330,033 A | 9/1943 | D'Aiello |
| 3,042,710 A | 7/1962 | Dickstein et al. |
| 3,197,318 A | 7/1965 | Halpern et al. |
| 3,203,915 A | 8/1965 | D'Aiello |
| 3,221,745 A | 12/1965 | Coover et al. |
| 3,427,250 A | 2/1969 | Haas et al. |
| 3,489,663 A | 1/1970 | Bayer et al. |
| 3,523,097 A | 8/1970 | Coover et al. |
| 3,557,185 A | 1/1971 | Ito et al. |
| 3,591,676 A | 7/1971 | Hawkins |
| 3,595,869 A | 7/1971 | Shuman |
| 3,677,989 A | 7/1972 | Jenkinson |

(Continued)

FOREIGN PATENT DOCUMENTS

| | | |
|---|---|---|
| CN | 102901754 A | 1/2013 |
| DE | 19508049 A1 | 9/1996 |

(Continued)

OTHER PUBLICATIONS

Takagi et al.: Kogyo Kagaku Zasshi, Reaction of Active Methylene Radicals with Formaldehyde. L. Synthesis of Diethyl Methylenemalonate, 1953, 56, pp. 901-903, English abstract.
McNab, Kirk-Othmer Encyclopedia of chemical Technology, Pyrolysis, Flash Vacuum, 2009, John Wiley & Sons, Inc., pp. 1-26.

(Continued)

*Primary Examiner* — Michael Bernshteyn
(74) *Attorney, Agent, or Firm* — Young Basile Hanlon & MacFarlane, P.C.

(57) ABSTRACT

The disclosure relates to compositions containing 1,1-di-carbonyl-substituted alkene compounds capable of preparing polymers having glass transition temperatures above room temperature. The present teaching also relates to polymers prepared 1,1-di-carbonyl-substituted alkene compounds which exhibit glass transition temperatures of 60° C. The disclosure also relate to methods for enhancing the glass transition temperatures of polymers prepared from 1,1-di-carbonyl-substituted alkene compounds.

18 Claims, 6 Drawing Sheets

(56) References Cited

U.S. PATENT DOCUMENTS

| | | |
|---|---|---|
| 3,758,550 A | 9/1973 | Eck et al. |
| 3,923,836 A | 12/1975 | Bender |
| 3,936,486 A | 2/1976 | Egger et al. |
| 3,940,362 A | 2/1976 | Overhurlts |
| 3,945,891 A | 3/1976 | Aal et al. |
| 3,966,562 A | 6/1976 | Mukushi et al. |
| 3,975,422 A | 8/1976 | Buck |
| 3,978,422 A | 8/1976 | Rheinfelder |
| 3,995,489 A | 12/1976 | Smith et al. |
| 4,001,345 A | 1/1977 | Gorton et al. |
| 4,004,984 A | 1/1977 | Margen |
| 4,018,656 A | 4/1977 | Rogers et al. |
| 4,035,243 A | 7/1977 | Katz et al. |
| 4,036,985 A | 7/1977 | Amato et al. |
| 4,046,943 A | 9/1977 | Smith et al. |
| 4,049,698 A | 9/1977 | Hawkins et al. |
| 4,056,543 A | 11/1977 | Ponticello |
| 4,079,058 A | 3/1978 | Ackermann et al. |
| 4,080,238 A | 3/1978 | Wolinski et al. |
| 4,083,751 A | 4/1978 | Choi et al. |
| 4,102,809 A | 7/1978 | Smith et al. |
| 4,105,688 A | 8/1978 | Arni et al. |
| 4,140,584 A | 2/1979 | Margen |
| 4,148,693 A | 4/1979 | Williamson |
| 4,154,914 A | 5/1979 | Kuraya |
| 4,160,864 A | 7/1979 | Ponticello et al. |
| 4,176,012 A | 11/1979 | Bryant |
| 4,186,058 A | 1/1980 | Katz et al. |
| 4,186,060 A | 1/1980 | Katz et al. |
| 4,198,334 A | 4/1980 | Rasberger |
| 4,224,112 A | 9/1980 | Childs |
| 4,229,263 A | 10/1980 | Childs |
| 4,236,975 A | 12/1980 | Childs |
| 4,237,297 A | 12/1980 | Rody et al. |
| 4,243,493 A | 1/1981 | Gruber et al. |
| 4,256,908 A | 3/1981 | Nishimura et al. |
| 4,282,067 A | 8/1981 | Katz et al. |
| 4,282,071 A | 8/1981 | Sherrod |
| 4,291,171 A | 9/1981 | Baum et al. |
| 4,313,865 A | 2/1982 | Teramoto et al. |
| 4,319,964 A | 3/1982 | Katz et al. |
| 4,329,479 A | 5/1982 | Yabutani et al. |
| 4,396,039 A | 8/1983 | Klenk et al. |
| 4,399,300 A | 8/1983 | Prange et al. |
| 4,411,740 A | 10/1983 | Flanigam et al. |
| 4,440,601 A | 4/1984 | Katz et al. |
| 4,440,910 A | 4/1984 | O'Connor |
| 4,443,624 A | 4/1984 | Prange et al. |
| 4,444,928 A | 4/1984 | Karrer |
| 4,450,067 A | 5/1984 | Angevine et al. |
| 4,503,074 A | 3/1985 | Friedman |
| 4,504,658 A | 3/1985 | Narisada et al. |
| 4,510,273 A | 4/1985 | Miura et al. |
| 4,517,105 A | 5/1985 | Laemmle et al. |
| 4,539,423 A | 9/1985 | Itatani et al. |
| 4,556,649 A | 12/1985 | Salzburg et al. |
| 4,560,723 A | 12/1985 | Millet et al. |
| 4,578,503 A | 3/1986 | Ishikawa et al. |
| 4,584,064 A | 4/1986 | Ciais et al. |
| 4,613,658 A | 9/1986 | Mathias et al. |
| 4,698,333 A | 10/1987 | Fauss et al. |
| 4,720,543 A | 1/1988 | McPherson et al. |
| 4,727,701 A | 3/1988 | Figari |
| 4,728,701 A | 3/1988 | Jarvis et al. |
| 4,736,056 A | 4/1988 | Smith et al. |
| 4,767,503 A | 8/1988 | Crescentini et al. |
| 4,769,464 A | 9/1988 | Sajtos |
| 4,783,242 A | 11/1988 | Robbins |
| 4,835,153 A | 5/1989 | Kabota et al. |
| 4,897,473 A | 1/1990 | Dombek |
| 4,914,226 A | 4/1990 | Di Trapani et al. |
| 4,931,584 A | 6/1990 | Bru-Magniez et al. |
| 4,932,584 A | 6/1990 | Yamazaki et al. |
| 5,021,486 A | 6/1991 | Galbo |
| 5,039,720 A | 8/1991 | Saatweber et al. |
| 5,064,507 A | 11/1991 | O'Donnell |
| 5,142,098 A | 8/1992 | Bru-Magniez et al. |
| 5,162,545 A | 11/1992 | Etzbach et al. |
| 5,210,222 A | 5/1993 | O'Murchu |
| 5,227,027 A | 7/1993 | Topper |
| 5,259,835 A | 11/1993 | Clark et al. |
| 5,284,987 A | 2/1994 | Sikkenga et al. |
| 5,292,937 A | 3/1994 | Manning et al. |
| 5,328,687 A | 4/1994 | Leung et al. |
| 5,312,864 A | 5/1994 | Wenz et al. |
| 5,334,747 A | 8/1994 | Steffen |
| 5,426,203 A | 6/1995 | Sohn et al. |
| 5,446,195 A | 8/1995 | Pacifici |
| 5,514,371 A | 5/1996 | Leung et al. |
| 5,514,372 A | 5/1996 | Leung et al. |
| 5,550,172 A | 8/1996 | Regula et al. |
| 5,565,525 A | 10/1996 | Morimoto et al. |
| 5,567,761 A | 11/1996 | Song |
| 5,575,997 A | 11/1996 | Leung et al. |
| 5,582,834 A | 12/1996 | Leung et al. |
| 5,614,650 A | 3/1997 | Sandler et al. |
| 5,624,669 A | 4/1997 | Leung et al. |
| 5,693,621 A | 12/1997 | Toepfer et al. |
| 5,817,742 A | 10/1998 | Toepfer et al. |
| 5,817,870 A | 10/1998 | Haas et al. |
| 5,886,219 A | 3/1999 | Steffen |
| 5,902,896 A | 5/1999 | Bauer |
| 5,952,407 A | 9/1999 | Rasoul et al. |
| 6,054,606 A | 4/2000 | Irie et al. |
| 6,069,261 A | 5/2000 | Hoffmann et al. |
| 6,096,848 A | 8/2000 | Gololobov et al. |
| 6,106,807 A | 8/2000 | Albayrak et al. |
| 6,143,352 A | 11/2000 | Clark et al. |
| 6,183,593 B1 | 2/2001 | Narang et al. |
| 6,210,474 B1 | 4/2001 | Romano, Jr. et al. |
| 6,211,273 B1 | 4/2001 | Bru-Magniez et al. |
| 6,225,038 B1 | 5/2001 | Smith et al. |
| 6,238,896 B1 | 5/2001 | Ozaki et al. |
| 6,245,933 B1 | 6/2001 | Malofsky et al. |
| 6,284,915 B2 | 9/2001 | Hirase et al. |
| 6,291,703 B1 | 9/2001 | Schaerfl et al. |
| 6,376,019 B1 | 4/2002 | Leung |
| 6,395,737 B1 | 5/2002 | Defossa et al. |
| 6,395,931 B1 | 5/2002 | Carvalho et al. |
| 6,413,415 B1 | 7/2002 | Weiss et al. |
| 6,420,468 B2 | 7/2002 | Bru-Magniez et al. |
| 6,440,461 B1 | 8/2002 | Bru-Magniez et al. |
| 6,512,023 B1 | 1/2003 | Malofsky et al. |
| 6,518,677 B1 | 2/2003 | Capote |
| 6,545,097 B2 | 4/2003 | Pinchuk et al. |
| 6,559,264 B1 | 5/2003 | Konig et al. |
| 6,610,078 B1 | 8/2003 | Bru-Magniez et al. |
| 6,613,934 B1 | 9/2003 | Jegelka et al. |
| 6,673,957 B2 | 1/2004 | Bartek et al. |
| 6,699,928 B2 | 3/2004 | Cobbley et al. |
| 6,716,355 B1 | 4/2004 | Hanemaaijer et al. |
| 6,750,298 B1 | 6/2004 | Bru-Magniez et al. |
| 6,794,365 B2 | 9/2004 | Al-Obeidi et al. |
| 6,841,064 B1 | 1/2005 | Weiss et al. |
| 6,936,140 B2 | 8/2005 | Paxton et al. |
| 7,070,675 B2 | 7/2006 | Schmidt et al. |
| 7,109,369 B2 | 9/2006 | Nose et al. |
| 7,208,621 B2 | 4/2007 | Nose et al. |
| 7,226,957 B1 | 6/2007 | Scranton et al. |
| 7,305,850 B2 | 12/2007 | Tonkovich et al. |
| 7,553,989 B2 | 6/2009 | Sawabe et al. |
| 7,603,889 B2 | 10/2009 | Cypes et al. |
| 7,610,775 B2 | 11/2009 | Tonkovich et al. |
| 7,649,108 B2 | 1/2010 | Schal et al. |
| 7,659,423 B1 | 2/2010 | McArdle |
| 7,663,000 B2 | 2/2010 | Dekkers et al. |
| 7,771,567 B2 | 8/2010 | Rives et al. |
| 7,829,738 B1 | 11/2010 | Brammer et al. |
| 7,900,558 B2 | 3/2011 | Yokoi |
| 8,425,999 B2 | 4/2013 | McArdle et al. |
| 8,609,885 B2 | 12/2013 | Malofsky et al. |
| 8,884,051 B2 | 11/2014 | Malofsky et al. |
| 9,108,914 B1 | 8/2015 | Malofsky et al. |
| 9,181,365 B2 | 11/2015 | Malofsky et al. |

(56) References Cited

U.S. PATENT DOCUMENTS

| | | | |
|---|---|---|---|
| 9,217,098 B1 | 12/2015 | Stevenson et al. | |
| 9,221,739 B2 | 12/2015 | Malofsky et al. | |
| 9,234,107 B2 | 1/2016 | Malofsky et al. | |
| 9,334,430 B1 | 5/2016 | Stevenson et al. | |
| 9,481,640 B2 | 11/2016 | McArdle et al. | |
| 9,752,059 B2* | 9/2017 | Malofsky | C09J 5/04 |
| 2001/0005572 A1 | 6/2001 | Lobo et al. | |
| 2001/0034300 A1 | 10/2001 | Yurugu et al. | |
| 2002/0035231 A1 | 3/2002 | Whitehouse et al. | |
| 2002/0143128 A1 | 10/2002 | Cabioch et al. | |
| 2002/0151629 A1 | 10/2002 | Buffkin et al. | |
| 2003/0096069 A1 | 5/2003 | D'Alessio | |
| 2003/0199655 A1 | 10/2003 | Yurugi et al. | |
| 2004/0057914 A1 | 3/2004 | Bonda et al. | |
| 2004/0076601 A1 | 4/2004 | Bru-Magniez et al. | |
| 2004/0082043 A1 | 4/2004 | Yadav et al. | |
| 2004/0220060 A1 | 11/2004 | Bartley et al. | |
| 2006/0167267 A1 | 7/2006 | Chorghade et al. | |
| 2006/0211809 A1 | 9/2006 | Kodemura et al. | |
| 2007/0043145 A1 | 2/2007 | Beck et al. | |
| 2007/0049655 A1 | 3/2007 | Yoshimune et al. | |
| 2007/0092483 A1 | 4/2007 | Pollock | |
| 2007/0120630 A1 | 10/2007 | Malofsky et al. | |
| 2007/0238872 A1 | 10/2007 | Sabesan | |
| 2008/0131618 A1 | 6/2008 | Nakamura et al. | |
| 2008/0160305 A1 | 7/2008 | Warren et al. | |
| 2008/0187655 A1 | 8/2008 | Markle et al. | |
| 2008/0227919 A9 | 9/2008 | Li et al. | |
| 2008/0241485 A1 | 10/2008 | Shimomura et al. | |
| 2008/0286333 A1 | 11/2008 | Kangas et al. | |
| 2009/0203861 A1 | 8/2009 | Lee et al. | |
| 2009/0263604 A1 | 10/2009 | Arai et al. | |
| 2010/0016508 A1 | 1/2010 | Sasagawa et al. | |
| 2010/0256720 A1 | 10/2010 | Overstreet et al. | |
| 2010/0286433 A1 | 11/2010 | Malofsky et al. | |
| 2010/0286438 A1 | 11/2010 | Malofsky et al. | |
| 2011/0015406 A1 | 1/2011 | Umentani et al. | |
| 2011/0024392 A1 | 2/2011 | Sato et al. | |
| 2011/0164322 A1 | 7/2011 | Morozumi et al. | |
| 2012/0083523 A1 | 4/2012 | Richard et al. | |
| 2012/0136130 A1 | 5/2012 | Takashima et al. | |
| 2012/0203021 A1 | 8/2012 | Friese et al. | |
| 2013/0019520 A1 | 1/2013 | Sello et al. | |
| 2013/0281580 A1 | 10/2013 | Malofsky et al. | |
| 2013/0303719 A1 | 11/2013 | Malofsky et al. | |
| 2013/0324754 A1 | 12/2013 | Bredsguard | |
| 2014/0058031 A1 | 2/2014 | Overbeek et al. | |
| 2014/0248485 A1 | 9/2014 | Malofsky et al. | |
| 2014/0275400 A1 | 9/2014 | Chen et al. | |
| 2014/0288230 A1 | 9/2014 | Malofsky et al. | |
| 2014/0329980 A1 | 11/2014 | Malofsky et al. | |
| 2015/0056879 A1 | 2/2015 | Malofsky et al. | |
| 2015/0104660 A1 | 4/2015 | Malofsky et al. | |
| 2015/0148480 A1 | 5/2015 | Ellison et al. | |
| 2015/0210894 A1 | 7/2015 | Malofsky et al. | |
| 2015/0303122 A1 | 10/2015 | Malofsky et al. | |
| 2015/0361283 A1 | 12/2015 | Malofsky et al. | |

FOREIGN PATENT DOCUMENTS

| | | | | |
|---|---|---|---|---|
| EP | 2768917 | A2 | 2/2009 | |
| FR | 2788516 | A1 | 7/2000 | |
| GB | 432628 | A | 7/1935 | |
| GB | 965676 | | 8/1964 | |
| GB | 965767 | | 8/1964 | |
| GB | 975733 | | 11/1964 | |
| JP | S56-081537 | A | 7/1981 | |
| JP | H02281013 | | 11/1993 | |
| JP | H08231564 | | 9/1996 | |
| JP | 09258448 | | 10/1997 | |
| JP | 2000199936 | A | 7/2000 | |
| JP | 2003201397 | A | 7/2003 | |
| JP | 2008174494 | | 1/2007 | |
| WO | 1999/046619 | | 9/1999 | |
| WO | 1999055394 | A1 | 11/1999 | |
| WO | 2007/120630 | A2 | 10/2007 | |
| WO | 2010/091975 | A1 | 8/2010 | |
| WO | 2010/129068 | A1 | 11/2010 | |
| WO | 2011/059104 | A1 | 5/2011 | |
| WO | 2011/161045 | A1 | 12/2011 | |
| WO | 2012/054616 | A2 | 4/2012 | |
| WO | 2012/054633 | A2 | 4/2012 | |
| WO | 2013/059473 | | 4/2013 | |
| WO | WO-2013059473 | A2 * | 4/2013 | C09J 133/06 |
| WO | 2013/066629 | | 5/2013 | |
| WO | 2013/149165 | A1 | 10/2013 | |
| WO | 2013/149168 | A1 | 10/2013 | |
| WO | 2013/149173 | A1 | 10/2013 | |

OTHER PUBLICATIONS

Block, "Diethyl bis (hydroxymethyl) malonate" Organic Syntheses, 1973, Coll. vol. 5, p. 381 [vol. 40, p. 27 (1960); Retrieved on Apr. 4, 2014 from internet: http://www.Orgsyn.org/content/pdfs/procedures/cv5p0381.pdf] p. 381, para 1.

Reddy et al. "An easy-to-use heterogeneous promoted zirconia catalyst for Knoevenagel condensation in liquid phase under solvent-free conditions." Journal of Molecular Catalysts A: Chemical 258 (2006) pp. 302-307.

M. Ware et al.: "DBU: An Efficient Catalyst for Knoeveganel Condensation under Solvent-free Condition," Bulletin of the Catalysis Society of India, (2007), vol. 6, pp. 104-106.

V. G. Nenajdenko et al.: "Reaction of 2-Methylene-1,3-Dicarbonyl Compounds Containing a CF3-Group with 1,3-Dienes," Tetrahedron, (2000), vol. 56, pp. 6549-6556.

J. S. Yadav et al.,: "Phosphane-Catalyzed Knoevenagel Condensation: a Facile Synthesis of a-Cyanoacrylates and a-Cyanoacrylonitriles," Eur, J, Org, Chem. (2004), pp. 546-551.

B. C. Ranu et al.: "Ionic Liquid as Catalyst and Reaction Medium—a Simple, Efficient and Green Procedure for Knoevenagel Condensation of Aliphatic and Aromatic Carbonyl Compounds Using a Task-Specific Basic Ionic Liquid," Euro. J. Org <http://Euro.J.Org>. Chem., (2006), pp. 3767-3770.

H, A, Oskooie et al.: "On Water: an Efficient Knoevenagel Condensation using 12- Tungstophosphoric Acid as a Reusable Green Catalyst," Synthetic Communications, (2006), vol. 36, pp. 2819-2823.

H. Jiang et al.: "Inorganic Zinc Salts Catalyzed Knoevenagel Condensation at Room Temperature without Solvent," Preparative Biochemistry & Biotechnology, (2009), vol. 39, pp. 194-200.

T. Doi et al.: "Synthesis of Dimethyl gloiosiphne A by Way of Palladium-Catalyzed Domino Cyclization," T. Ora <htto://T.Ora>. Chem., (2007), vol. 72, pp. 3667-3671.

H. Jung et al,: "New and General Methods for the Synthesis of Arylmethylene Bis(3- Hydroxy- 2-Cyclohexene-1-0nes) and Xanthenediones by EDDA and ln(OTf)3-Catalyzed One-Pot Domino Knoevenagei/Michael or Koevenagei/Michaei/Cyclodehydration Reactions," Bull. Korean Chem. Soc. (2009) vol. 30, No. 9, pp. 1989-1995.

P. Klemarczyk: "Adhesion Studies of Mixtures of Ethyl Cyanoacrylate with a Difunctional Cyanoacrylate Monomer and with other Electron-deficient Olefins," J. Adhesion, (1999), vol. 69, pp. 293-306.

P. Klemarwczyk: "A General Synthesis of 1,1 Disubstituted Electron Deficient Olefins and their Polymer Properties," Polymer,— (1998), vol. 39, No. I, pp. 173-181.

Gill, Charansingh, et al. "Knoevenagel condensation in neutral media: A simple and efficient protocol for the synthesis of electrophilic alkenes catalyzed by anhydrous ferric sulphate with remarkable reusability." Bulletin of the Catalysis Society of India 7 (2008): 153-157.

P, Ballesteros et al.: "D 1-tert-Butyl Methylenemalonate [Propanedioic Acid, Methylene-, bis( 1,1- dimethylethyl)ester]," Organic Syntheses. Coli. (1990), vol. 7, p. 142; (1986) vol. 64, p. 63.

A. M. Vetrova et al.: "Improvement of the Thermal Stability of Cyanoacrylate Adhesives," Polymer Science, Series D, (2009), vol. 2, No. 1, pp. 27-30.

(56) References Cited

OTHER PUBLICATIONS

A. C. Cope: "Condensation Reactions. I. The Condensation of Ketones with Cyanoacetic Esters and the Mechanism of the Knoevenagel Reaction," Condensation of Ketones with Cyanoacetic Esters, (1937), vol. 59, pp. 2327-2330.

G. Lai et al.: "Ionic Liquid Functionalized Silica Gel: Novel Catalyst and Fixed Solvent," Tetrahedron Letters (2006), vol. 47, pp. 6951-6953.

J. R. Harjani et al.: "Lewis Acidic Ionic Liquids for the Synthesis of Electrophilic Alkenes; via the Knoevenaqel Condensation," Tetrahedron Letters, (2002), vol. 43, pp. 1127-1130.

P. Ballesteros et al.: "Synthesis of Dl-tent-Butyl Methylenemalonate, a Sterically Hindered 1,1-Dicarbonyl Alkene," J. Ora <htto://J.Ora>. Chem, (1983), vol. 48, pp. 3603-3605.

M. Matziari et al. Active Methylene Phosphinic Peptides: A new Diversification Approach Organic Letters 2006 vol. 8, No. 11 pp. 2317-2319 May 5, 2006.

Zaragoza Dorwald, Side Reactions in Organic Synthesis, 2005, Wiley-VCH Verlag GmbH & Co., KgaA, Weinheim, Preface. p. IX.

K. Okamura and T. Date, A Facile Conversion of Ethoxydihydropyrans to 4-Cyanoethylisoxazoles, J. Heterocyclic Chem. 33, 383 (1996).

Yamauchi et al. Tetrahedron Asymetry 12, (2001), 3113-3118.

Cristoph Schotes et al. "Cu(I)- and C(II)- Catalyzed Cyclo- and Michael Addition Reactions of Unsaturated [beta]-Ketoesters" The Journal of Organic Chemistry, vol. 76, No. 14 dated Jul. 15, 2011 p. 5862-5866.

Alejandro Bugarin et al. "Efficient direct [alpha]-methylenation of carbonyls mediated by dissopropylammonium trifluoroacetate", Chemical Communications, vol. 46, No. 10 dated Jan. 25, 2010.

H. Hoffman et al. "Preparation and Selected Reaction of tery-Butyl 2-Methylene-3-oxoalkanoates" Chem. Ber., vol. 124 dated Jan. 1, 1991, pp. 2475-2480.

M. Yamauchi et al. "Reactivity of 2-Methylene-1, 3-dicarbonyl Compounds. 1,3-Dipolar Cycloaddition Reaction with Ethyl Diazoacetate", Chem. Pham. Bull., vol. 49, No. 12, dated Jun. 25, 2001, pp. 1638-1639.

Lawrence N J et al. "Reaction of Baylis-Hillman products with Swern and Dess-Martin oxidants", Tetrahedron Letters, Pergamon, GB, vol. 42 No. 23 dated Jun. 4, 2001, pp. 3939-3941.

Juliana Vale et al. "Efficient [alpha]-Methylenation of Carbonyl Compounds in Ionic Liquids at Room Temperature", SYNLETT, vol. 2009, No. 01, Jan. 1, 2009 (Jan. 1, 2009), pp. 75-78, XP055170349, ISSN: 0936-5214, DOI: 10.1055/s-0028-1087389 *table 2; compound 3 *.

P. Breton et al., "New Poly(Methylidudene Malonate 2.1.2) Nanoparticles: Recent Developments", Targeting of Drugs 4, NATO ASI Series, vol. 273, pp.161-172, 1994.

Limouzin et al., "Anionic Polymerization of n-Butyl Cyanoacrylate in Emulsion and Miniemulsion" Macromolecules, vol. 36, 2003, pp. 667-674.

McCoy, M. "A New Way to Stick" Chemical & Engineering News, vol. 92, Issue 26, Jun. 30, 2014, pp. 17-18, paragraph [2].

Bachman et al., "Diethyl Methylenemalonate" Contirbution from the Research Laboratories of the Eastman Kodak Company, May 17, 1939, pp. 493-501.

"Knoevenagel reaction on a molecular sieve", Li Qifang et al., Chinese Science Bulletin, vol. 12, pp. 914-917. (1988).

"Knoevenagel Condensation Over Acidic Zeolite", Zuo Bojun et al., Chinese Journal of Catalysis, vol. 23 (6), pp. 555-558. (2002).

"Comparison of the catalytic activity of MOFs and zeolites in Knoevenagel condensation", Maksym Opanasenko, et al., Catalysis Science & Technology, vol. 3 p. 500-507. (2013).

Corey et al. "Total Synthesis of Gibberellic Acid. A Simple Synthesiss of a Key Intermediate", J. Am. Chem. Soc. 1982, 104, 6129-6130.

Krishna et al. "Stereodefined Access to 3-Deoxy Sugars Through a Tandem Baylis-Hillman and Lewis Acid Catalyzed Sequence", European Journal of Organic Chemistry, 2010, 813-817.

March, *Advanced Organic Chemistry*, 2d Ed, section 0-25, pp. 365-367, 1977, McGraw Hill, New York, New York.

Morrison and Boyd, *Organic Chemistry*, $4^{th}$ Ed., pp. 831 and 836-838, 1983, Allyn Bacon, Inc., Boston, MA.

Otera et al., "Esterification: Methods, Reactions, and Applications", $2^{nd}$ Ed., pp. 55-58, 2010, Wiley-VCH Verlag Gmbh & Co. KGaA. Weinheim, Germany.

"Esterification of Sludge Palm Oil Using Trifluromethanesulfonic Acid for Preparation of Biodiesel Fuel", Korean Journal of Chemical Engineering, Jun. 2013, vol. 30, issue 6, pp. 1229-1234.

Transsesterification of diethyl malonate with Benzyl Alcohol Catalyzed by Modified Zirconia: Kinetic Study, Journal of Molecular Catalysis A: Chemical, vol. 391, Sep. 2014, pp. 55-65.

Olah et al., "Superelectrophilic Solvation," Accounts of Chemical Research, Apr. 2004, vol. 37, No. 4.

Kütt et al., "Equilibrium Acidities of Superacids," Journal of Organic Chemistry, vol. 76, No. 2, 2011, pp. 391-395, published on the web Dec. 17, 2010.

Larras et al. Synthesis and micellization of amphiphilic poly(ethylene oxide)-block-poly(methylidene malonate 2.1.2.) diblock copolymers Macromol. Rapid Commun. dated2000, vol. 21, pp. 1089-1029.

Yamauchi et al. *A Facile Conversion of Ethoxydihydropyrans to 4-Cyanoethylisoxazoles*, Mar.-Apr. 1996, pp. 383-387.

* cited by examiner

COMPOSITIONS CONTAINING 1,1-DI-CARBONYL-SUBSTITUTED ALKENE COMPOUNDS FOR PREPARING POLYMERS HAVING ENHANCED GLASS TRANSITION TEMPERATURES

CROSS-REFERENCE TO RELATED APPLICATION(S)

The present application is a continuation of U.S. application Ser. No. 15/783,181 published as U.S. Pat. No. 9,890,227 filed on Oct. 13, 2017, which is a continuation of U.S. application Ser. No. 15/088,340 published as U.S. Pat. No. 9,790,295 filed on Apr. 1, 2016, which is a continuation of U.S. application Ser. No. 14/859,992 published as U.S. Pat. No. 9,315,597 filed on Sep. 21, 2015, which claims benefit of U.S. provisional application No. 62/219,194 filed on Sep. 16, 2015, and is a continuation in part of Patent Cooperation Treaty application number PCT/US2015/048846 filed on Sep. 8, 2015, which claims benefit of U.S. provisional application No. 62/047,283 filed on September 8, 2014; said U.S. application Ser. No. 14/859,992 claims benefit of U.S. provisional application No. 62/215,360 filed on Sep. 8, 2015 and is a continuation in part of U.S. application Ser. No. 14/810,741 published as U.S. Pat. No. 9,279,022 filed on Jul. 28, 2015, which claims benefit of U.S. provisional application No. 62/186,479 filed on Jun. 30, 2015 and claims benefit of U.S. provisional application No. 62/047,328 filed on Sep. 8, 2014; said U.S. application Ser. No. 14/859,992 is a continuation in part of U.S. application Ser. No. 14/789,178 published as U.S. Pat. No. 9,249,265 filed on Jul. 1, 2015, which claims benefit of U.S. provisional application No. 62/182,076 filed on Jun. 19, 2015; and said U.S. application Ser. No. 14/859,992 is a continuation in part of U.S. application Ser. No. 14/814,961 published as U.S. Pat. No. 9,416,091 filed on Jul. 31, 2015, which claims benefit of U.S. provisional application 62/111,919 filed on Feb. 4, 2015 and claims benefit of U.S. provisional application 62/198,844 filed on Jul. 30, 2015.

FIELD

Disclosed are compositions containing 1,1-disubstituted alkene compounds for preparing polymers having enhanced glass transition temperatures, polymeric compositions prepared from such compositions and methods of enhancing the glass transition temperatures of polymers prepared from 1,1-disubstituted alkene compounds.

BACKGROUND 1,1-disubstituted alkene compounds find use in a number of applications such as adhesives, coatings, composites and the like. 1,1-disubstituted alkene compounds, with two ester substituents on the alkene double bond, are commonly known as methylene malonates. These compounds have been known since the 19th century and in the mid-20th century a number of researchers worked with these compounds, see D'Alelio U.S. Pat. No. 2,330,033; Coover U.S. Pat. Nos. 3,221,745 and 3,523,097; Halpern U.S. Pat. No. 3,197,318; and Ponticello U.S. Pat. Nos. 4,056,543 and 4,160,864, all incorporated herein by reference in their entirety for all purposes. Despite this work the 1,1-disubstituted alkene compounds have not been commercialized. The disclosed processes for the preparation of these compounds produce a number of by-products that negatively impact the stability of the desired products which precludes the reasonable use of the compounds. In addition, some of the by-products and starting materials are difficult to separate from the desired compounds. 1,1-disubstituted alkene compounds polymerize rapidly at room temperature under mild conditions in presence of nucleophilic or basic initiating species, which render them both useful, as well as, present problems with their stability. The problems with the processes and the products of the processes were not fully appreciated until Malofsky et al. studied the compounds and processes and developed ways to produce these compounds without the presence of starting materials and by-products that negatively impact their stability. Malofsky et. al. developed methods for enhancing the stability of such compounds while facilitating cure of the compounds at room temperature upon demand, see Malofsky et al. U.S. Pat. Nos. 8,609,885; 8,884,405; US2014/0329980; and US 2015/0073110; all incorporated herein by reference in their entirety for all purposes.

The work of Malofsky et al. resulted in commercial interest in 1,1-disubstituted alkene compounds for use in a variety of applications. For many uses the 1,1-disubstituted alkene compounds prepared in the Malofsky et al. patents and applications provide advantageous properties. Many of the 1,1-disubstituted alkene compounds prepared in the Malofsky et al. patents and applications exhibit glass transition temperatures near or below room temperature. Although the low glass transition temperatures are advantageous for a number of applications, to broaden the application scope for these compounds it is desirable to develop 1,1-disubstituted alkene compounds and compositions that can prepare polymers with higher glass transition temperatures.

Thus, what is needed are 1,1-disubstituted alkene compounds that are capable of forming polymers with glass transition temperatures of 60° C., more preferably above 80° C., even more preferably above 100° C. and even more preferably above 120° C. What are also needed are methods for enhancing the glass transition temperatures of polymers prepared from 1,1-disubstituted alkene compounds.

SUMMARY

The disclosure relates to compositions containing 1,1-disubstituted alkene compounds capable of preparing polymers having glass transition temperatures above room temperature. The present teaching also relates to polymers prepared from 1,1-disubstituted alkene compounds which exhibit glass transition temperatures above room temperature. The disclosure also relates to methods for enhancing the glass transition temperatures of polymers prepared from 1,1-disubstituted alkene compounds. Disclosed herein are compositions comprising one or more first 1,1-disubstituted alkene compounds having two carbonyls bonded to the 1 carbon atom wherein each carbonyl group independently has a hydrocarbyl group bonded to the carbonyl groups through a direct bond or a heteroatom wherein the one or more first 1,1-disubstituted alkene compounds have one or more of the hydrocarbyl groups comprising an aryl group, aralkyl group, alkaryl group with the aryl group bonded to the 1 carbon atom, a cycloalkyl group, an alkyl group with a cycloalkyl group on the 1 carbon atom, or a branched alkyl group wherein the 1 carbon atom is a tertiary or the 1 and 2 carbon atoms are secondary wherein the composition is polymerizable and contains a sufficient amount of the first 1,1-disubstituted alkene compounds such that a polymer prepared from the composition exhibits a glass transition (Tg) temperature of greater than 35° C. In some embodiments the compositions further comprise one or more second 1,1-disubstituted alkene compounds wherein the hydrocarbyl groups prepare homopolymers having a glass transition temperature of less than 60° C. In some embodiments the one or more second 1,1-disubstituted alkene compounds contain hydrocarbyl groups which prepare homopolymers having a glass transition temperature about 30 to less than 60° C. or less. In some embodiments the composition prepares polymers with a Tg of 60° C. or greater. In some embodiments the compositions contain 10 percent by weight or greater of the first 1,1-disubstituted alkene compounds. 1,1-disubstituted alkene compounds are compounds wherein a central carbon atom is doubly bonded to another carbon atom to form an alkylene group, for example an ethylene group. The central carbon atom is further bonded to two carbonyl groups. Each carbonyl group is bonded to a hydrocarbyl group through a direct bond or hetero atom. With respect to the hydrocarbyl groups bonded to the carbonyl groups the 1 carbon atom refers to the carbon atom bonded to the carbonyl group through a direct bond or hetero atom. With respect to the hydrocarbyl groups bonded to the carbonyl groups the number of the carbon atom (for instance 2 or 3) refers to the number of the carbon atom from the direct bond or a heteroatom bonded to the carbonyl group. In some embodiments disclosed is a composition comprising about 10 weight percent or greater of one or more first 1,1-disubstituted alkene compounds wherein each carbonyl group independently has a hydrocarbyl group bonded to the carbonyl groups by a direct bond, an oxygen atom, a nitrogen atom or a sulfur atom wherein one or more of the hydrocarbyl groups comprise an aryl group, aralkyl group, alkaryl group with the aryl group bonded to the 1 or 2 carbon atom, a cycloalkyl group, an alkyl group with a cycloalkyl group on the 1 or 2 carbon atom, or a branched alkyl group wherein the 1 carbon atom is a tertiary or the 1 and 2 carbon atoms are secondary; and about 10 weight percent or greater of one or more second 1,1-disubstituted alkene compounds wherein each carbonyl group independently has a hydrocarbyl group bonded to the carbonyl groups by a direct bond, an oxygen atom, a nitrogen atom or a sulfur atom and the hydrocarbyl groups are selected such that homopolymers prepared from the second 1,1-disubstituted alkenes exhibit glass transition temperatures of less than 60° C.

Such compounds are illustrated by the formula 1 or 2:

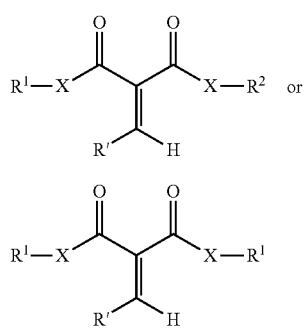

wherein: $R^1$ is separately in each occurrence a hydrocarbyl group comprising an aryl group, aralkyl group, alkaryl group with the aryl group bonded to the 1 carbon atom, a cycloalkyl group, an alkyl group with a cycloalkyl group on the 1 carbon atom, or a branched alkyl group wherein the 1 carbon atom is a tertiary or the 1 and 2 carbon atoms are secondary; $R^2$ is, separately in each occurrence a hydrocarbyl group wherein a homopolymer prepared therefrom exhibits a Tg of less than 60° C.; R' is separately in each occurrence hydrocarbyl or hydrogen and X is a heteroatom or a direct bond. The remainder of the one or more 1,1-disubstituted alkene compounds can be one or more of any other 1,1-disubstituted alkene compounds.

In some embodiments the remainder of the one or more 1,1-disubstituted alkene compounds contain hydrocarbyl groups, which correspond to $R^1$, which comprise straight or branched chained alkyl groups having one secondary carbon atom or a tertiary carbon atom not directly connected to the carbonyl carbon or to a heteroatom connected to a carbonyl carbon atom, examples of such other compounds include those corresponding to formula 3.

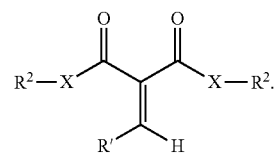

Such compositions may further include one or more compounds containing the core unit of two or more 1,1-disubstituted alkene compounds wherein one of the carbonyl groups of each compound is bonded through oxygen atoms to a polyvalent hydrocarbyl group, wherein the composition is crosslinked when polymerized. Such compounds can be represented by formula 4:

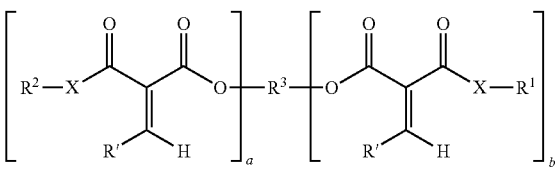

wherein, R', $R^1$, $R^2$ and X are as described hereinbefore; $R^3$ is separately in each occurrence a polyvalent hydrocarbon group; a is separately in each occurrence an integer of 1 or more; b is separately in each occurrence an integer of 0 or more wherein the sum of a and b is 2 or greater and the number of valences of $R^3$ is equal to the sum of a and b.

In some embodiments the composition comprises one or more first 1,1-disubstituted alkene compounds having at least two hydrocarbyl groups. Such compounds have at least one hydrocarbyl group which is an aryl group, aralkyl group, alkaryl group with the aryl group bonded to the 1 or 2 carbon atom, a cycloalkyl group, an alkyl group with a cycloalkyl group on the 1 or 2 carbon atom, or a branched alkyl group wherein the 1 carbon atom is a tertiary or the 1 and 2 carbon atoms are secondary. Such compounds further have least one hydrocarbyl group which is alkyl with a primary 1 carbon atom or a secondary 1 carbon atom and a primary 2 carbon atom, alkenyl with a primary 1 carbon atom or a secondary 1 carbon atom and a primary 2 carbon atom, alkaryl wherein the aryl group is bonded to a carbon atom which is 3 or more carbon atoms from the direct bond, or heteroatom, alkyl group with a cycloalkyl group bonded to a carbon atom which is 3 or more carbon atoms from the direct bond, or heteroatom, or a polyalkylene ether. In some embodiments disclosed are compositions wherein the one or more first 1,1-disubstituted alkene compounds have at least one hydrocarbyl group which is an aryl group, aralkyl group, alkaryl group with the aryl group bonded to the 1 or 2 carbon atom, a cycloalkyl group, an alkyl group with a cycloalkyl group on the 1 or 2 carbon atom, or a branched alkyl group wherein the 1 carbon atom is a tertiary or the 1 and 2 carbon atoms are secondary and at least one hydrocarbyl group which is $C_{1-8}$ alkyl with a primary 1 carbon atom or a secondary 1 carbon atom and a primary 2 carbon atom.

In some embodiments the composition comprises about 10 mole percent or more of one or more first 1,1-disubstituted alkene compounds wherein the Tg of the copolymers prepared therefrom is 60° C. or greater. In some embodiments the composition comprises about 25 mole percent by weight or more of the one or more of the first 1,1-disubstituted alkene compounds wherein the Tg of the copolymers prepared therefrom is 80° C. or greater. In some embodiments the composition comprises about 45 mole percent or more of the one or more first 1,1-disubstituted alkene compounds wherein the Tg of the copolymers prepared therefrom is 100° C. or greater. In some embodiments the composition comprises about 65 mole percent or more of the one or more first 1,1-disubstituted alkene compounds wherein the Tg of the copolymers prepared therefrom is 120° C. or greater.

In some embodiments the compositions comprise one or more first 1,1-disubstituted alkene compounds and one or more second 1,1-disubstituted alkene compounds which exhibit a purity of 95 mole percent or greater, have one mole percent or less of the analogous 1,1-disubstituted alkane, 1 mole percent or less of an impurity containing a dioxane group, about 1 mole percent of less of any impurity having the alkene group replaced by an analogous hydroxyalkyl group wherein mole percent is based on the total moles in the 1,1-disubstituted alkene compound.

In some embodiments disclosed are compositions wherein copolymers prepared from the composition exhibit a glass transition temperature determined according to the formula:

$$Tg = Y*W + V \pm 15° \text{ wherein}$$

Y is the mole percent of the first 1,1-disubstituted alkene compound;
W is the Tg of the first 1,1-disubstituted alkene compound minus the Tg of the second 1,1-disubstituted alkene compound: and
V is the Tg of the second 1,1-disubstituted alkene compound;
wherein Tg is expressed in ° C.

Disclosed herein are polymers prepared from any of the monomer compositions disclosed herein, for instance from one or more first 1,1-disubstituted alkene compounds. Disclosed are copolymers prepared from one or more first 1,1-disubstituted alkene compounds and one or more second 1,1-disubstituted alkene compounds. The disclosure further relates to polymers prepared from about 10 weight percent or greater of one or more first 1,1-disubstituted alkene compounds wherein each carbonyl group independently has a hydrocarbyl group bonded to the carbonyl groups by a direct bond, an oxygen atom, nitrogen atom or a sulfur atom wherein one or more of the hydrocarbyl groups comprising an aryl group, aralkyl group, alkaryl group with the aryl group bonded to the 1 or 2 carbon atom, a cycloalkyl group, an alkyl group with a cycloalkyl group on the 1 or 2 carbon atom, or a branched alkyl group wherein the 1 carbon atom is a tertiary or the 1 and 2 carbon atoms are secondary; and about 10 weight percent or greater of one or more second 1,1-disubstituted alkene compounds wherein each carbonyl group independently has a hydrocarbyl group bonded to the carbonyl groups by a direct bond, or a heteroatom and the hydrocarbyl groups are selected such that homopolymers prepared from the second 1,1-disubstituted alkenes exhibit glass transition temperatures of less than 60° C. The polymer may include one or more compounds containing two or more core units of 1,1-disubstituted alkene compounds wherein one of the carbonyl groups of each compound is bonded through oxygen atoms to a polyvalent hydrocarbyl group, wherein the polymer is crosslinked. Disclosed are copolymers wherein the second 1,1-disubstituted alkenes have hydrocarbyl groups which are alkyl with a primary 1 carbon atom or a secondary 1 carbon atom and a primary 2 carbon atom, alkenyl with a primary 1 carbon atom or a secondary 1 carbon atom and a primary 2 carbon atom, alkaryl wherein the aryl group is bonded to a carbon atom which is 3 or more carbon atoms from the direct bond or heteroatom, alkyl group with a cycloalkyl group bonded to a carbon atom which is 3 or more carbon atoms from the direct bond or heteroatom, or a polyalkylene ether.

In some embodiments, disclosed are polymers which comprise 100 mole percent by weight of one or more of the first 1,1-disubstituted alkene compounds wherein at least one of the hydrocarbyl groups comprise fenchyl, menthyl, isobornyl, furfuryl, phenethyl, or adamantyl groups wherein the polymer exhibits a glass transition temperature of 120° C. or greater. In some embodiments, the polymers include the one or more first 1,1-disubstituted alkene compounds which have only one of the hydrocarbyl groups comprising an aryl group, aralkyl group, alkaryl group with the aryl group bonded to the 1 carbon atom, a cycloalkyl group, an alkyl group with a cycloalkyl group on the 1 carbon atom, or a branched alkyl group wherein the 1 carbon atom is a tertiary or the 1 and 2 carbon atoms are secondary and at least one other hydrocarbyl group is alkyl with a primary 1 carbon atom or a secondary 1 carbon atom and a primary 2 carbon atom, alkenyl with a primary 1 carbon atom or a secondary 1 carbon atom and a primary 2 carbon atom, alkaryl wherein the aryl group is bonded to a carbon atom which is 3 or more carbon atoms from the direct bond or heteroatom, alkyl group with a cycloalkyl group bonded to a carbon atom which is 3 or more carbon atoms from the direct bond or heteroatom, or a polyalkylene ether. These polymers are prepared from compounds represented by Formula 1 and include all embodiments of $R^1$, $R^2$, R' and X.

In another embodiment, disclosed is a method comprising contacting one or more first 1,1-disubstituted alkene compounds with one or more second 1,1-disubstituted alkene compounds with a polymerization initiator under conditions to polymerize the composition and the glass transition temperature of the resulting polymer is increased over the glass transition temperature of a homopolymer of the one or more second 1,1-disubstituted alkene compounds. In some embodiments about 10 mole percent or greater of one or more first 1,1-disubstituted alkene compounds is present in the compounds contacted.

In some embodiments the invention is a composition comprising one or more first 1,1-disubstituted alkene compounds wherein each carbonyl group independently has a hydrocarbyl group bonded to the carbonyl groups by a direct bond or a heteroatom wherein one or more of the hydrocarbyl groups comprise a menthyl, fenchyl, isobornyl, furfuryl, phenethyl, 2-phenyl propyl or adamantyl.

The compositions disclosed are capable of preparing polymers based on 1,1-disubstituted alkene compounds having glass transition temperatures of greater than room temperature, some compositions prepare polymers having glass transition temperatures of about 60° C. or greater, some compositions prepare polymers having glass transition temperatures of about 80° C. or greater, some compositions prepare polymers having glass transition temperatures of about 100° C. or greater and some compositions prepare polymers having glass transition temperatures of about 120° C. or greater. The polymers disclosed herein exhibit glass transition temperatures of about 60° C. or greater, some polymers exhibit glass transition temperatures of about 80° C. or greater, some polymers exhibit glass transition temperatures of about 100° C. or greater and some polymers exhibit glass transition temperatures of about 120° C. or greater. The methods disclosed facilitate preparation of 1,1-disubstituted alkene compound based compositions that can deliver polymers having desired or targeted glass transition temperatures. The methods disclosed allow the tailoring of polymers of 1,1-disubstituted alkene compounds to have desired or targeted glass transition temperatures. The compositions and methods of the invention facilitate the use of 1,1-disubstituted alkene compounds in a broader variety of applications, for instance adhesives and coatings where greater structural rigidity and modulus are desired, components for optical fibers, resins and other adhesive and coating applications where exposure to high temperature is expected, and the like.

DETAILED DESCRIPTION

Figure 1:
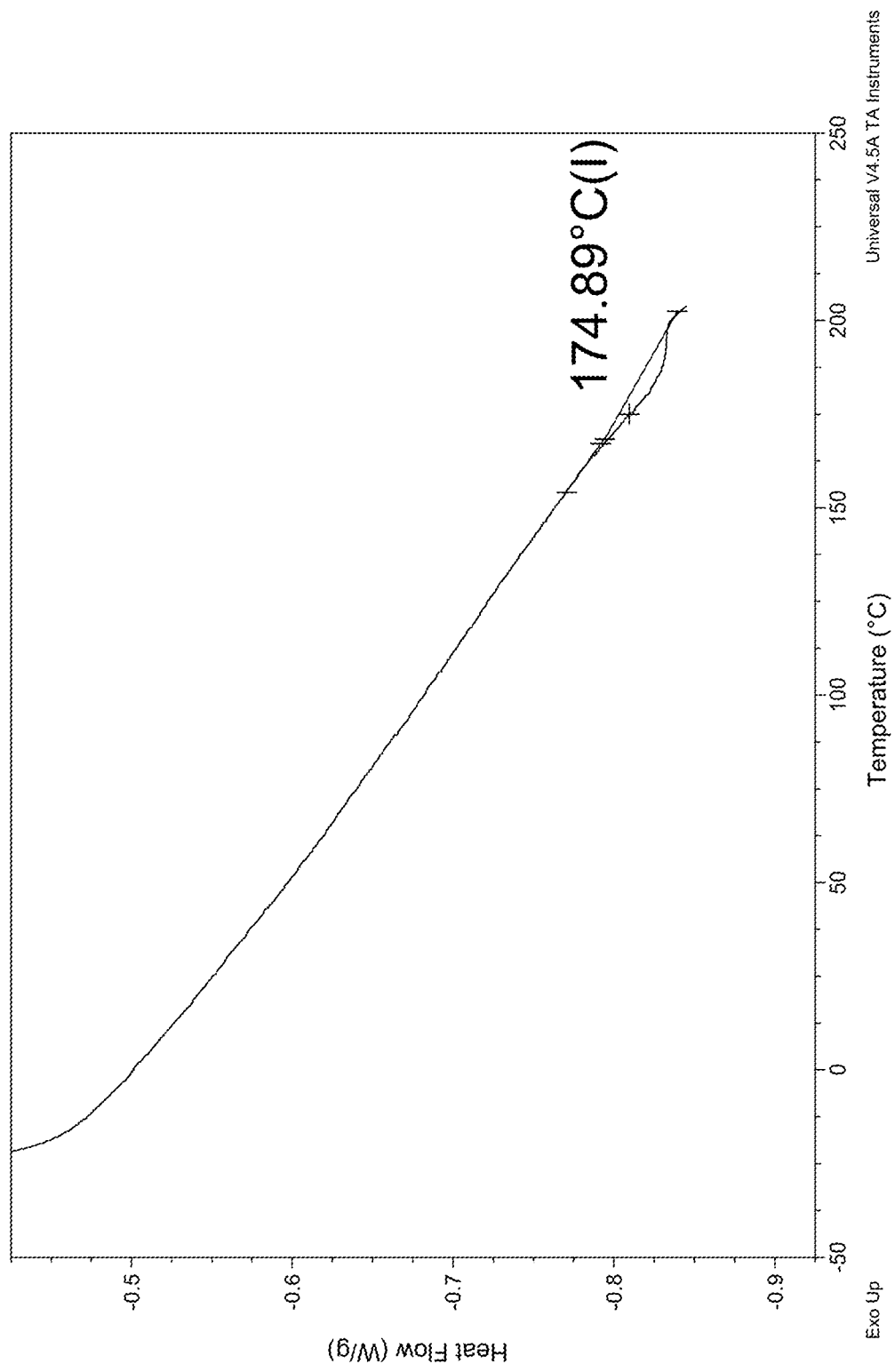
FIG. 1 is a DSC trace of the polymer based on fenchyl ethyl methylene malonate.

The explanations and illustrations presented herein are intended to acquaint others skilled in the art with the disclosure, its principles, and its practical application. The specific embodiments of the present disclosure as set forth are not intended as being exhaustive or limiting of the disclosure. The scope of the disclosure should be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The disclosure relates to a curable composition, which can be cured on demand at ambient conditions using one or more first 1,1-disubstituted alkene compounds. In general the disclosed compositions contain 1,1-disubstituted alkene compounds having two carbonyl groups on the 1 carbon atom wherein hydrocarbyl groups are bonded to a portion of the carbonyl groups so as to enhance the glass transition temperature of polymers containing such first 1,1-disubstituted alkene compounds. In this context the 1 carbon atom refers to the carbon of the alkene group bonded to carbonyl groups, alkene 1 carbon atom. The first 1,1-disubstituted alkene compounds may have one or more of the hydrocarbyl groups bonded to the carbonyl groups, which enhance the glass transition temperature of polymers containing the first 1,1-disubstituted alkene compounds. In essence a sufficient amount of such compounds are contained in compositions containing the first 1,1-disubstituted alkene compounds to result in polymers having desired or targeted glass transition temperatures of 60° C. or greater.

1,1-disubstituted alkene compounds are compounds wherein a central carbon atom is doubly bonded to another carbon atom to form an alkylene group, for example an ethylene group. The central carbon atom is further bonded to two carbonyl groups. Each carbonyl group is bonded to a hydrocarbyl group through a direct bond or a heteroatom. Where the hydrocarbyl group is bonded to the carbonyl group through a direct bond, a keto group is formed. Where the hydrocarbyl group is bonded to the carbonyl group through a heteroatom an ester, amide or thioester is formed, in a preferred embodiment the hydrocarbyl group is bonded to the carbonyl group through an oxygen atom, such that an ester group is formed. The 1,1-disubstituted alkene compounds useful herein may have all ester, amide or thioester groups, all keto groups or a mixture thereof. Compounds with all ester groups are preferred due to the flexibility of synthesizing a variety of such compounds.

One or more as used herein means that at least one, or more than one, of the recited components may be used as disclosed. Residual content of a component refers to the amount of the component present in free form or reacted with another material, such as a polymer. Typically, the residual content of a component can be calculated from the ingredients utilized to prepare the component or composition. Alternatively, it can be determined utilizing known analytical techniques. Heteroatom as used herein means nitrogen, oxygen, and sulfur, more preferred heteroatoms include nitrogen and oxygen with oxygen most preferred. Hydrocarbyl as used herein refers to a group containing one or more carbon atom backbones and hydrogen atoms, which may optionally contain one or more heteroatoms. Where the hydrocarbyl group contains heteroatoms, the heteroatoms may form one or more functional groups well known to one skilled in the art. Hydrocarbyl groups may contain cycloaliphatic, aliphatic, aromatic or any combination of such segments. The aliphatic segments can be straight or branched. The aliphatic and cycloaliphatic segments may include one or more double and/or triple bonds. Included in hydrocarbyl groups are alkyl, alkenyl, alkynyl, aryl, cycloalkyl, cycloalkenyl, alkaryl and aralkyl groups. Cycloaliphatic groups may contain both cyclic portions and noncyclic portions. Hydrocarbylene means a hydrocarbyl group or any of the described subsets having more than one valence, such as alkylene, alkenylene, alkynylene, arylene, cycloalkylene, cycloalkenylene, alkarylene and aralkylene. Valence as used herein means a covalent bond between a hydrocarbyl or hydrocarbylene group and another group such as a carbonyl, oxygen, nitrogen or sulfur group or atom. As used herein percent by weight or parts by weight refer to, or are based on, the weight of the compositions unless otherwise specified.

Unless defined otherwise, all technical and scientific terms used herein have the meaning commonly understood by a person skilled in the art to which this disclosure belongs. The following references provide one of skill with a general definition of many of the terms used in this disclosure: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

A preferred class of 1,1-disubstituted alkene compounds are the methylene malonates which refer to compounds having the core unit represented by Formula 4:

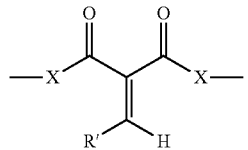

The term "monofunctional" refers to 1,1-substituted alkene compounds or methylene malonates having only one core unit. The term "difunctional" refers to 1,1-disubstituted alkene compounds or a methylene malonates having two core units bound through a hydrocarbylene linkage between one oxygen atom on each of two core units. The term "multifunctional" refers to refers to 1,1-disubstituted alkene compounds or methylene malonates having more than one core units which form a chain through a hydrocarbylene linkage between one oxygen atom on each of two adjacent core units. The terms "latent acid-forming impurities" or "latent acid-forming impurity" refer to any impurity that, if present along with the recovered 1,1-disubstituted alkene compounds or methylene malonates, will with time be converted to an acid. The acid formed from these impurities tends to result in overstabilization of the 1,1-disubstituted alkene compounds, thereby reducing the overall quality and reactivity of the compounds. The term "ketal" refers to molecule having a ketal functionality; i.e. a molecule containing a carbon bonded to two —OR groups, where O is oxygen and R represents any hydrocarbyl group, for example an alkyl group. As used herein, the term "stabilized," e.g., in the context of "stabilized" 1,1-disubstituted alkene compounds or compositions comprising same, refers to the tendency of the compounds (or their compositions) to substantially not polymerize with time, to substantially not harden, form a gel, thicken, or otherwise increase in viscosity with time, and/or to substantially show minimal loss in cure speed (i.e., cure speed is maintained) with time. As used herein, the term "shelf-life," e.g., as in the context of 1,1-disubstituted alkene compounds having an improved "shelf-life," refers to the 1,1-disubstituted alkene compounds which are stabilized for a given period of time, e.g., 1 month, 6 months, or even 1 year or more.

Exemplary hydrocarbyl groups comprise straight or branched chain alkyl, straight or branched chain alkenyl, straight or branched chain alkynyl, cycloalkyl, alkyl substituted cycloalkyl, aryl, aralkyl, alkaryl, wherein the hydrocarbyl groups may contain one or more heteroatoms in the backbone of the hydrocarbyl group and may be substituted with a substituent that does not negatively impact the ultimate function of the compounds or polymers prepared from the compounds. Exemplary substituents include alkyl, halo, alkoxy, alkylthio, hydroxyl, nitro, cyano, azido, carboxy, acyloxy, and sulfonyl groups; more preferred substituents include alkyl, halo, alkoxy, alkylthio, and hydroxyl groups, and halo, alkyl and alkoxy are even more preferred. Alkaryl means an alkyl group with an aryl group bonded thereto. Aralkyl means an aryl group with an alkyl group bonded thereto and include alkylene bridged aryl groups such as diphenyl methylene or propylene groups. Aryl includes groups containing more than one aromatic ring. Cycloalkyl includes groups containing one or more rings including bridged rings. Alkyl substituted cycloalkyl means a cycloalkyl group having one or more alkyl groups bonded to the cycloalkyl ring. Exemplary hydrocarbyl groups are $C_{1-20}$ hydrocarbyl groups. Exemplary hydrocarbyl groups with heteroatoms in the backbone are alkyl ethers having one or more alkyl ether groups, alkylene oxy groups, heteroatom containing aryl groups, heteroatom containing cycloalkyl groups, and the like. Preferred alkyl ether groups are ethoxy, propoxy, and butoxy. Preferably such compounds contain from about 1 to about 100 alkyleneoxy groups and more preferably about 1 to about 40 alkyleneoxy groups and more preferably from about 1 to about 10 alkyleneoxy groups. Preferably the hydrocarbyl groups comprise $C_{1-15}$ straight or branched chain alkyl, $C_{2-15}$ straight or branched chain alkenyl, $C_{5-18}$ cycloalkyl, $C_{6-24}$ alkyl substituted cycloalkyl, $C_{4-18}$ aryl, $C_{4-20}$ aralkyl and $C_{4-20}$ aralkyl groups. More preferably the hydrocarbyl groups comprise $C_{1-8}$ straight or branched chain alkyl, $C_{5-12}$ cycloalkyl, $C_{6-12}$ alkyl substituted cycloalkyl, $C_{4-18}$ aryl, $C_{4-20}$ aralkyl and $C_{4-20}$ alkaryl groups. Preferred alkyl groups are include methyl, ethyl, propyl, isopropyl, butyl, tertiary butyl, hexyl, ethyl hexyl, with methyl and ethyl even more preferred. Preferred cycloalkyl groups include cyclohexyl and fenchyl. Preferred alkyl substituted cycloalkene groups include menthyl and isobornyl. Most preferred hydrocarbyl groups attached to the carbonyl groups include methyl, ethyl, propyl, isopropyl, butyl, tertiary butyl, hexyl, ethyl hexyl, cyclohexyl, fenchyl, menthyl, phenyl-propyl, furfuryl, phenethyl, adamantyl and isobornyl.

The 1,1-disubstituted alkene compounds can be prepared as disclosed in Malofsky et al., U.S. Pat. Nos. 8,609,885 and 8,884,051; Malofsky et al. WO 2013/059473 and Sullivan et al. U.S. Ser. No. 14/814,961 filed Jul. 31, 2015, all incorporated herein by reference in their entirety for all purposes. In some embodiments the 1,1-disubstituted alkenes are prepared in the form of 1,1-disubstituted alkenes having methyl or ethyl, preferably ethyl, hydrocarbyl groups connected to the carbonyl groups. There after one or more of the hydrocarbyl groups are replaced via the process disclosed in Sullivan et al. U.S. Ser. No. 14/814,961 filed Jul. 31, 2015. Exemplary 1,1-disubstituted alkene compounds correspond to Formula 1, 2 or 3 as disclosed hereinbefore.

Exemplary hydrocarbyl groups, the presence of which increase the Tg of polymers formed therefrom include aryl groups, aralkyl groups, alkaryl groups with the aryl group bonded to the 1 carbon atom, cycloalkyl groups, alkyl groups with a cycloalkyl group on the 1 carbon atom, or branched alkyl groups wherein the 1 carbon atom is a tertiary or the 1 and 2 carbon atoms are secondary. In certain embodiments the hydrocarbyl groups the presence of which increase the Tg of polymers formed therefrom include a cyclic terpene, alkyl substituted cycloalkyl, adamantyl, furfuryl, tertiary butyl groups, or mixtures thereof. In certain embodiments, the hydrocarbyl groups, the presence of which increase the Tg of polymers formed therefrom include fenchyl, menthyl, cyclohexyl, 2-phenyl propyl, or isobornyl groups. Exemplary 1,1-disubstituted alkenes having one or more hydrocarbyl groups on the carbonyl carbons which increase the glass transition temperatures of polymers prepared therefrom are illustrated by Formulas 1 and 2 presented hereinbefore. In certain embodiments the substituents on the hydrocarbyl groups on the 1,1-disubstituted alkenes may include alkyl, halo, alkoxy, alkylthio, hydroxyl, nitro, cyano, azido, carboxy, acyloxy, and sulfonyl groups; more preferred substituents include alkyl, halo, alkoxy, alkylthio, and hydroxyl groups, with halo, alkyl and alkoxy are even more preferred. In certain embodiments $R^1$ is separately in each occurrence $C_{4-15}$ branched chain alkyl wherein the 1 carbon atom is a tertiary or the 1 and 2 carbon atoms are secondary, $C_{4-15}$ branched chain alkenyl wherein the 1 carbon atom is a tertiary or the 1 and 2 carbon atoms are secondary, $C_{5-18}$ cycloalkyl, $C_{6-24}$ alkyl substituted cycloalkyl, $C_{4-18}$ aryl, $C_{4-20}$ aralkyl or $C_{4-20}$ aralkyl groups. In certain embodiments $R^1$ is separately in each occurrence $C_{4-8}$ branched chain alkyl wherein the 1 carbon atom is a tertiary or the 1 and 2 carbon atoms are secondary, $C_{5-12}$ cycloalkyl, $C_{6-12}$ alkyl substituted cycloalkyl, $C_{4-18}$ aryl, $C_{4-20}$ aralkyl or $C_{4-20}$ alkaryl groups. In certain embodiments $R^1$ is separately in each occurrence tertiary butyl, fenchyl, menthyl, cyclohexyl, 2-phenyl propyl, furfuryl, adamantyl and isobornyl.

Preferably $R^2$ is separately in each occurrence straight or branched chain alkyl having a primary 1 carbon atom or a secondary 1 carbon atom and primary 2 carbon atom, straight or branched chain alkenyl having a primary 1 carbon atom or a secondary 1 carbon atom and primary 2 carbon atom, straight or branched chain alkynyl having a primary 1 carbon atom or a secondary 1 carbon atom and primary 2 carbon atom, cycloalkyl, alkyl substituted cycloalkyl, aryl, aralkyl, or alkaryl, wherein the hydrocarbyl groups may contain one or more heteroatoms in the backbone of the hydrocarbyl group and may be substituted with a substituent that does not negatively impact the ultimate function of the compounds or polymers prepared from the compounds. In certain embodiments such substituents may include alkyl, halo, alkoxy, alkylthio, hydroxyl, nitro, cyano, azido, carboxy, acyloxy, and sulfonyl groups; more preferred substituents include alkyl, halo, alkoxy, alkylthio, and hydroxyl groups, with halo, alkyl and alkoxy are even more preferred. In certain embodiments $R^2$ is separately in each occurrence $C_{1-15}$ straight or branched chain alkyl having a primary 1 carbon atom or a secondary 1 carbon atom and primary 2 carbon atom, $C_{2-15}$ straight or branched chain alkenyl a primary 1 carbon atom or a secondary 1 carbon atom and primary 2 carbon atom, $C_{5-18}$ cycloalkyl, $C_{6-24}$ alkyl substituted cycloalkyl, $C_{4-18}$ aryl, $C_{4-20}$ aralkyl or $C_{4-20}$ alkaryl groups. In certain embodiments $R^2$ is separately in each occurrence $C_{1-8}$ straight or branched chain alkyl having a primary 1 carbon atom or a secondary 1 carbon atom and primary 2 carbon atom, $C_{5-12}$ cycloalkyl, $C_{6-12}$ alkyl substituted cycloalkyl, $C_{4-18}$ aryl, $C_{4-20}$ aralkyl or $C_{4-20}$ alkaryl groups. In certain embodiments $R^2$ is separately in each occurrence methyl, ethyl, propyl, isopropyl, butyl, tertiary butyl, hexyl, fenchyl, menthyl, cyclohexyl, phenyl propyl or isobornyl. Preferably R' is hydrogen, alkyl or alkylene group. Preferably R' is hydrogen or $C_{1-10}$ alkyl or alkylene. More preferably R' is hydrogen of $C_{1-4}$ alkyl or alkylene. R' is more preferably hydrogen or $C_{1-4}$ alkyl. Most preferably R' is hydrogen. In the embodiment where R' is hydrogen the compounds are commonly referred to a methylene malonates.

In the polymerizable compositions the hydrocarbyl groups that do not increase the glass transition temperatures of polymers prepared therefrom, can be any other hydrocarbyl groups. In some embodiments it may be desirable that such hydrocarbyl groups if homopolymerized, prepare polymers having a glass transition temperature of less than 60° C., preferably between about 30 to about 59° C. Exemplary hydrocarbyl groups that meet these criteria include occurrence alkyl with a primary 1 carbon atom or a secondary 1 carbon atom and primary 2 carbon atom, alkenyl with a primary 1 carbon atom or a secondary 1 carbon atom and primary 2 carbon atom, alkaryl wherein the aryl group is bonded to a carbon atom which is 3 or more carbon atoms from X, alkyl group with a cycloalkyl group bonded to a carbon atom which is 3 or more carbon atoms from the X, or a polyalkylene ether. In some embodiments such hydrocarbyl groups include straight chain $C_{1-8}$ alkyl groups with a primary 1 carbon atom or a secondary 1 carbon atom and primary 2 carbon atom, straight chain $C_{1-8}$ alkenyl groups with a primary 1 carbon atom or a secondary 1 carbon atom and primary 2 carbon atom, alkoxy groups, polyalkylene ether groups and the like. In certain embodiments the hydrocarbyl groups may be methyl or ethyl. In formulas 1 to 3 in some embodiments $R^2$ is separately in each occurrence alkyl with a primary 1 carbon atom or a secondary 1 carbon atom and primary 2 carbon atom, alkenyl with a primary 1 carbon atom or a secondary 1 carbon atom and primary 2 carbon atom, alkaryl wherein the aryl group is bonded to a carbon atom which is 3 or more carbon atoms from X, alkyl group with a cycloalkyl group bonded to a carbon atom which is 3 or more carbon atoms from the X, or a polyalkylene ether. In some embodiments $R^2$ is separately in each occurrence straight chain $C_{1-8}$ alkyl groups with a primary 1 carbon atom or a secondary 1 carbon atom and primary 2 carbon atom, straight chain $C_{1-8}$ alkenyl groups with a primary 1 carbon atom or a secondary 1 carbon atom and primary 2 carbon atom, alkoxy groups, polyalkylene ether groups and the like. In some embodiments $R^2$ is separately in each occurrence methyl or ethyl. In some embodiments X is nitrogen, or oxygen sulfur. In some embodiments X is nitrogen, or oxygen. In some embodiments X is oxygen.

The 1,1-disubstituted alkenes can be in the form of diesters, diamides, dithioesters wherein both hydrocarbyl groups are bonded to carbonyl groups through heteroatom, diketones, both hydrocarbyl groups are bonded to carbonyl groups through a direct bond, or keto-esters, ketoamides or ketothioesters wherein one hydrocarbyl group is bonded to a carbonyl group through a heteroatom and the other through a direct bond, or mixtures thereof.

Disclosed are compositions containing the first 1,1-disubstituted alkenes the presence of which in copolymers of 1,1-disubstituted alkenes, increase glass transition temperatures of polymers prepared containing a primary 1 carbon atom or a secondary 1 carbon atom and primary 2 carbon atom. In essence the inclusion of the first 1,1-disubstituted alkenes in a copolymer increases the glass transition temperature of the copolymers formed over the glass transition temperatures of polymers and copolymers prepared only from the second 1,1-disubstituted alkenes. The hydrocarbyl groups on the carbonyl carbons impact the glass transition temperature (Tg) of polymers prepared from the 1,1-disubstituted 1 alkenes. Tg as used herein can be measured using differential scanning calorimetry on a sample of about 0.5-20.0 mg. The sample is heated at a rate of about 10° C./min and then cooled at a rate of about 20° C./min. To enhance the Tg a sufficient amount of one or more first 1,1-disubstituted alkenes is included in polymerizable compostions to increase the glass transition temperatures of copolymers prepared therefrom. The increase in Tg is compared to polymers or copolymers prepared from the second 1,1-disubstituted alkenes. Disclosed are compositions which contain the first 1,1-disubstituted alkenes and polymers prepared containing the first 1,1-disubstituted alkenes. The compositions disclosed herein allow the preparation of polymerizable compositions and polymers with targeted Tg's. By selecting appropriate 1,1-disubstituted alkenes and the amounts thereof the glass transition temperature of polymers prepared therefrom can be controlled. Generally compositions containing 100 percent of one or more first 1,1-disubstituted alkenes results in polymers with the highest Tg's. The one or more first 1,1-disubstituted alkenes may have one or more of the hydrocarbyl groups which increase the resulting polymers Tg on the carbonyl groups. In monofunctional first 1,1-disubstituted alkenes one or both of the hydrocarbyl groups on the carbonyl carbons which increase the Tg of the resulting polymers may be present. In certain embodiments only one of the hydrocarbyl groups on the carbonyl carbons of the first 1,1-disubstituted alkenes which increase the Tg of the resulting polymers may be present as such compounds positively impact the Tg of the resulting polymers and such compounds are easier to synthesize. Nevertheless compositions disclosed herein may contain monofunctional first 1,1-disubstituted alkenes with both of the hydrocarbyl groups on the carbonyl carbons which increase the Tg of the resulting polymers. In multifunctional first 1,1-disubstituted alkenes, one or more, up to all, of the hydrocarbyl groups, which increase the Tg of the resulting polymers may be present on the carbonyl carbons. In some embodiments, the one or more first 1,1-disubstituted alkene compounds have at least one hydrocarbyl group which is an aryl group, aralkyl group, alkaryl group with the aryl group bonded to the 1 or 2 carbon atom, a cycloalkyl group, an alkyl group with a cycloalkyl group on the 1 or 2 carbon atom, or a branched alkyl group wherein the 1 carbon atom is a tertiary or the 1 and 2 carbon atoms are secondary and at least one hydrocarbyl group which is alkyl with a primary 1 carbon atom or a secondary 1 carbon atom and a primary 2 carbon atom, alkenyl with a primary 1 carbon atom or a secondary 1 carbon atom and a primary 2 carbon atom, alkaryl wherein the aryl group is bonded to a carbon atom which is 3 or more carbon atoms from the direct bond or heteroatom, alkyl group with a cycloalkyl group bonded to a carbon atom which is 3 or more carbon atoms from the direct bond or heteroatom, a polyalkylene ether. In some embodiments, the one or more first 1,1-disubstituted alkene compounds have at least one hydrocarbyl group which is an aryl group, aralkyl group, alkaryl group with the aryl group bonded to the 1 or 2 carbon atom, a cycloalkyl group, an alkyl group with a cycloalkyl group on the 1 or 2 carbon atom, or a branched alkyl group wherein the 1 carbon atom is a tertiary or the 1 and 2 carbon atoms are secondary and at least one hydrocarbyl group which is $C_{1-8}$ alkyl with a primary 1 carbon atom or a secondary 1 carbon atom and a primary 2 carbon atom. In some embodiments wherein the first 1,1-disubstituted alkene has different hydrocarbyl groups connected to carbonyl groups, at least one hydrocarbyl group functions to increase Tg as disclosed herein and the other may be a methyl or ethyl group and in some embodiments may be ethyl. The 1,1-disubstituted alkenes can also be multifunctional having more than one core unit and alkene group. The multifunctional 1,1-disubstituted alkenes comprise two or more 1,1-disubstituted alkene groups linked by the residue of polyfunctional polyol which is a polyvalent hydrocarbylene. The polyvalent hydrocarbylene group can be any hydrocarbylene group that can be used in the preparation of a polyol. The polyvalent hydrocarbylene group can influence the glass transition temperature of polymers prepared from 1,1-disubstituted alkenes containing such multifunctional 1,1 disubstituted-1-alkenes. Such group is also illustrated by $R^3$ in the previous formulas. Polyvalent hydrocarbylene groups which enhance the Tg of polymers prepared from mixtures containing such multifunctional 1,1-disubstructed alkenes include hydrocarbylene groups containing one or more arylene groups, cycloalkylene groups, aralkyl groups and the like. In certain embodiments such polyvalent hydrocarbylene groups include the residue of bisphenol A (4,4'-(propane-2,2-diyl) diphenyl), bisphenol F (2,2'-methylenediphenyl), aliphatic polyester polyols, aromatic polyester polyols, alkane diols, cyclohexyl dimethanol, benzene dimethanol and the like. Exemplary multifunctional 1,1-disubstituted alkenes are illustrated by Formula 4 disclosed hereinbefore.

In the context of Formula 4, preferably the sum of a and b is 2 to about 10 and more preferably 2 to about 5. In exemplary embodiments $R^3$ is separately in each occurrence straight or branched chain alkylene, straight or branched chain alkenylene, cycloalkylene, alkyl substituted cycloalkylene, arylene, aralkylene, or alkarylene, wherein the hydrocarbylene groups may contain one or more heteroatoms in the backbone of the hydrocarbylene group and may be substituted with a substituent that does not negatively impact the ultimate function of the compounds or polymers prepared from the compounds. Exemplary substituents are those disclosed as useful with respect to $R^1$. In certain embodiments $R^3$ is separately in each occurrence $C_{1-15}$ straight or branched chain alkylene, $C_{2-15}$ straight or branched chain alkenylene, $C_{5-18}$ cycloalkylene, $C_{6-24}$ alkyl substituted cycloalkylene, $C_{4-18}$ arylene, $C_{4-20}$ aralkylene or $C_{4-20}$ alkarylene groups. In certain embodiments $R^3$ is separately in each occurrence $C_{1-8}$ straight or branched chain alkylene, $C_{5-12}$ cycloalkylene, $C_{6-12}$ alkyl substituted cycloalkylene, $C_{4-18}$ arylene, $C_{4-20}$ aralkylene or $C_{4-20}$ alkarylene groups.

The presence of multifunctional 1,1-disubstituted alkenes in polymerizable compositions may function to crosslink polymers prepared therefrom. Crosslinking may further increase the glass transition temperature of the resulting polymers. In some embodiments the multifunctional 1,1-disubstituted alkenes are present in a sufficient amount to increase the glass transition temperature of the resulting polymers. In some embodiments the multifunctional 1,1-disubstituted alkenes are present in an amount of about 1 weight percent or greater, more preferably about 5 weight percent or greater and most preferably about 15 weight percent or greater. In some embodiments the multifunctional 1,1-disubstituted alkenes may be present in an amount of 100 weight percent or less. In some embodiments the multifunctional 1,1-disubstituted alkenes may be present in an amount of about 30 weight percent or less or about 15 weight percent or less. The multifunctional 1,1-disubstituted alkenes can be the first multifunctional 1,1-disubstituted alkenes, the second 1,1-disubstituted alkenes or a mixture thereof. In some embodiments wherein the multifunctional 1,1-disubstituted alkenes are present as crosslinkers they are the second 1,1-disubstituted alkenes.

The 1,1-disubstituted alkene compounds are preferably prepared using a method, which results in a sufficiently high purity so that it can be polymerized. The purity of the 1,1-disubstituted alkene compound may be sufficiently high so that 70 mole percent or more, preferably 80 mole percent or more, more preferably 90 mole percent or more, even more preferably 95 mole percent or more, and most preferably 99 mole percent or more of the 1,1-disubstituted alkene compound is converted to polymer during a polymerization process. The purity of the 1,1-disubstituted alkene compound preferably is about 85 mole percent or more, preferably about 90 mole percent or more, even more preferably about 93 mole percent or more, even more preferably about 95 mole percent or more, even more preferably about 97 mole percent or more, and most preferably about 99 mole percent or more, based on the total moles of the 1,1-disubstituted alkene compound. If the 1,1-disubstituted alkene compound includes the analogous 1,1-disubstituted alkane impurity it should preferably be about 10 mole percent or less, or more preferably about 1 mole percent or less. The concentration of any impurities containing a dioxane group preferably is about 2 mole percent or less, more preferably about 1 mole percent or less, even more preferably about 0.2 mole percent or less, and most preferably about 0.05 mole percent or less, based on the total moles of the 1,1-disubstituted alkene compound. The total concentration of any impurity having the alkene group replaced by an analogous hydroxyalkyl group (e.g., by a Michael addition of the alkene with water) preferably is about 3 mole percent or less, more preferably about 1 mole percent or less, even more preferably about 0.1 mole percent or less, and most preferably about 0.01 mole percent or less, based on the total moles in the 1,1-disubstituted alkene compound. Preferred 1,1-disubstituted alkene compounds are prepared by a process including one or more (e.g., two or more) steps of distilling a reaction product or an intermediate reaction product (e.g., a reaction product or intermediate reaction product of a source of formaldehyde and a malonic acid ester). The 1,1-disubstituted alkenes having the recited purities positively impact the glass transition temperature of the polymers prepared therefrom.

The glass transition temperature of compositions containing can be predicted based on the formula $$Tg = Y*W + V \pm 15°\text{ wherein}$$

Y is the weight percent of the first 1,1-disubstituted alkene compound;
W is the Tg of the first 1,1-disubstituted alkene compound minus the Tg of the second 1,1-disubstituted alkene compound: and
V is the Tg of the second 1,1-disubstituted alkene compound;
wherein Tg is expressed in ° C. The first 1,1-disubstituted alkene compound used in any embodiment to enhance the Tg of a copolymer as disclosed herein must exhibit a Tg of its homopolymer of greater than the target Tg. This is important to recognize when utilizing this formula. A number of other factors can impact the glass transition temperature of a polymer prepared from the 1,1-disubstituted alkenes, including molecular weight, amount of multifunctional monomers, amount of impurities present, polydispersity, tacticity and the packing of the polymer chains. For this reason the actual glass transition that can be determined as disclosed herein may be about 15° C. less or greater than that predicted by the formula.

The disclosure contained herein provides a way to tailor a polymerizable composition or polymer to exhibit a desired glass transition temperature. By selection of the first and second 1,1-disubstituted alkenes, the relative amounts of each and the amount of multifunctional 1,1-disubstituted present as a crosslinker a target glass transition temperature may be achieved. In general, if from about 5 to about 15 weight percent of a multifunctional 1,1-disubstituted alkene is present the glass transition temperature is increased from about 10 to about 15° C. This understanding allows the preparation of a number of new monomer compositions and polymers. In some embodiments, the polymerizable composition comprises about 10 mole percent or more of one or more first 1,1-disubstituted alkene compounds wherein the Tg of the copolymers prepared therefrom is 60° C. or greater. In some embodiments wherein the Tg of the copolymers prepared therefrom is 60° C. or greater about 1 mole percent or greater, or about 10 mole percent or greater of one or more second 1,1-disubstituted alkene compounds may be present. In such embodiments up to about 90 mole percent of one or more second 1,1-disubstituted alkene compounds may be present. In some embodiments, the polymerizable composition comprises about 25 mole percent or more of the one or more first 1,1-disubstituted alkene compounds, wherein the Tg of the copolymers prepared therefrom is 80° C. or greater. In some embodiments wherein the Tg of the copolymers prepared therefrom is 80° C. or greater about 1 mole percent or greater, or about 10 mole percent or greater of one or more second 1,1-disubstituted alkene compounds may be present. In such embodiments up to about 75 mole percent of one or more second 1,1-disubstituted alkene compounds may be present. In some embodiments, the polymerizable composition comprises about 45 mole percent or more of the one or more first 1,1-disubstituted alkene compounds wherein the Tg of the copolymers prepared therefrom is 100° C. or greater. In some embodiments wherein the Tg of the copolymers prepared therefrom is 100° C. or greater about 1 mole percent or greater, or about 10 mole percent or greater of one or more second 1,1-disubstituted alkene compounds may be present. In such embodiments up to about 55 mole percent of one or more second 1,1-disubstituted alkene compounds may be present. In some embodiments, the polymerizable composition, a composition, which comprises about 65 mole percent or more of the one or more first 1,1-disubstituted alkene compounds wherein the Tg of the copolymers prepared therefrom is 120° C. or greater. In some embodiments wherein the Tg of the copolymers prepared therefrom is 120° C. or greater about 1 mole percent or greater, or about 10 mole percent or greater of one or more second 1,1-disubstituted alkene compounds may be present. In such embodiments up to about 35 mole percent of one or more second 1,1-disubstituted alkene compounds may be present. Disclosed are new polymers prepared from these compositions.

In some embodiments new polymerizable compositions and polymers prepared therefrom comprise one or more first 1,1-disubstituted alkene compounds which contain one or more hydrocarbyl groups comprising menthyl, fenchyl, isobornyl, furfuryl, cyclohexyl, phenethyl, benzyl, tertiary butyl, 2-phenyl propyl and, or adamantyl. Homopolymers prepared from these first 1,1-disubstituted alkene compounds exhibit high glass transition temperatures. Compositions containing one or more one or more first 1,1-disubstituted alkene compounds which contain one or more hydrocarbyl groups comprising menthyl, fenchyl, isobornyl, furfuryl, cyclohexyl, phenethyl, benzyl, tertiary butyl, 2-phenyl propyl and, or adamantyl and one or more multifunctional 1,1-disubstituted alkene compounds are disclosed, wherein the one or more multifunctional 1,1-disubstituted alkenes can be one or more first multifunctional 1,1-disubstituted alkenes, one or more second multifunctional 1,1-disubstituted alkenes or mixtures thereof.

Disclosed herein are a number of new compounds comprising one or more first 1,1-disubstituted alkene compounds wherein each carbonyl group independently has a hydrocarbyl group bonded to the carbonyl groups by a direct bond, or a heteroatom wherein one or more of the hydrocarbyl groups comprise a menthyl, fenchyl, isobornyl, furfuryl, phenethyl, 2-phenyl propyl or adamantyl the one or more first 1,1-disubstituted alkenes correspond to one of formulas 1 or 2

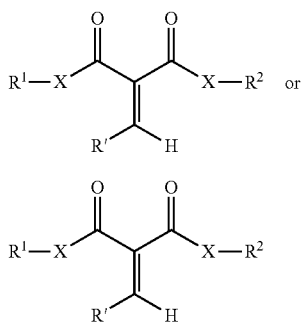

wherein: $R^1$ is separately in each occurrence a menthyl, fenchyl, isobornyl, furfuryl, phenethyl, 2-phenyl propyl or adamantyl; $R^2$, X and R' are as previously disclosed. Also disclosed are polymers prepared from these first 1,1-disubstituted alkenes, homopolymers prepared from these first 1,1-disubstituted alkenes, and polymers prepared from these first 1,1-disubstituted alkenes and multifunctional 1,1-disubstituted alkenes, which may be multifunctional first 1,1-disubstituted alkenes, multifunctional second 1,1-disubstituted alkenes or mixtures thereof.

Disclosed is a method comprising contacting one or more of the first 1,1-disubstituted alkene compounds disclosed herein with one or more second 1,1-disubstituted alkene compounds disclosed herein with a polymerization initiator under conditions to polymerize the composition and the glass transition temperature of the resulting polymer is increased over the glass transition temperature of a homopolymer of the one or more second 1,1-disubstituted alkene compounds. In some embodiments about 10 mole percent or greater of the first 1,1-disubstituted alkene compounds is present. This method can be utilized with any composition disclosed herein.

The polymerizable compositions disclosed herein can be polymerized by exposing the composition to free radical polymerization conditions or to anionic polymerization conditions. Free radical polymerization conditions are well known to those skilled in the art such as disclosed in U.S. Pat. No. 6,458,956 incorporated herein by reference. In certain embodiments the polymerizable compositions are exposed to anionic polymerization conditions. The polymerizable compositions are contacted with any anionic polymerization initiator or with any nucleophilic material. As the 1,1-disubstituted alkenes are highly electrophilic contact with any nucleophilic material can initiate anionic polymerization. Anionic polymerization is commonly referred to as living polymerization because the terminal portion of the polymeric chains are nucleophilic and will react with any unreacted 1,1-disubstituted alkenes they come into contact with. Thus the polymerizable composition will continue until all available unreacted 1,1-disubstituted alkenes polymerize or the polymerizing mixture is subjected to a quenching step. In a quenching step the mixture is contacted with an acid which terminates the polymeric chain ends and stops further polymerization. The polymerization can proceed at any reasonable temperature including at ambient temperatures, from about 20 to 35° C., depending on ambient conditions. The polymerization can be performed in bulk, without a solvent or dispersant, or in a solvent or dispersant.

According to certain embodiments, a suitable polymerization initiator can generally be selected from any agent that can initiate polymerization substantially upon contact with a selected polymerizable composition. In certain embodiments, it can be advantageous to select polymerization initiators that can induce polymerization under ambient conditions and without requiring external energy from heat or radiation. In embodiments wherein the polymerizable composition comprises one or more 1,1-disubstituted alkene compounds, a wide variety of polymerization initiators can be utilized including most nucleophilic initiators capable of initiating anionic polymerization. Exemplary initiators include alkali metal salts, alkaline earth metal salts, ammonium salts, amines, halides (halogen containing salts), metal oxides, and mixtures containing such salts or oxides. Exemplary anions for such salts include anions based on halogens, acetates, benzoates, sulfur, carbonates, silicates and the like. The mixtures containing such compounds can be naturally occurring or synthetic. Specific examples of exemplary polymerization initiators for 1,1-disubstituted alkene compounds can include glass beads (being an amalgam of various oxides including silicon dioxide, sodium oxide, and calcium oxide), ceramic beads (comprised of various metals, nonmetals and metalloid materials), clay minerals (including hectorite clay and bentonite clay), and ionic compounds such as sodium silicate, sodium benzoate, and calcium carbonate. Other polymerization initiators can also be suitable including certain plastics (e.g., ABS, acrylic, and polycarbonate plastics) and glass-fiber impregnated plastics. Additional suitable polymerization initiators for such polymerizable compositions are also disclosed in U.S. Patent App. Publication No. 2015/0073110, which is hereby incorporated by reference. In some embodiments the polymerization initiator may be encapsulated using any encapsulation method compatible with the polymerization of the 1,1-disubstituted alkenes. In some embodiments the encapsulated initiator (activation agent) may be as disclosed in Stevenson et al. Ser. No. 14/725,532 filed May 29, 2015 incorporated herein by reference in its entirety for all purposes.

Polymerization can be terminated by contacting the polymeric mixture with an anionic polymerization terminator. In some embodiments the anionic polymerization terminator is an acid. In some embodiments it is desirable to utilize a sufficient amount of the acid to render the polymerization mixture slightly acidic, preferably having a pH of less than 7, more preferably less than about 6. Exemplary anionic polymerization terminators include, for example, mineral acids such as methane sulfonic acid, sulfuric acid, and phosphoric acid and carboxylic acids such as acetic acid and trifluoroacetic acid.

The polymerizable compositions may be polymerized in bulk, which is in the absence of a solvent or dispersant, in a solution or in an emulsion. Polymerization in bulk can be performed by contacting the polymerizable composition which may include any of the other ingredients disclosed herein with a suitable substrate and an activator and allowing the composition to polymerize.

The polymerizable compositions may be prepared by emulsion polymerization. For example the polymerizable compositions may be prepared by the process disclosed in Stevenson et al., U.S. Ser. No. 14/789,178 filed Jul. 1, 2015 incorporated herein by reference in its entirely for all purposes. Disclosed in Stevenson et al., is a process comprising the steps of: agitating a mixture including: about 25 weight percent or more of a carrier liquid, a surfactant (e.g., an emulsifier) and one or more monomers to form micelles of the one or more monomers in the carrier liquid, wherein the one or more monomers includes one or more 1,1-disubstituted alkenes; reacting an activator with at least one of the monomers in the micelle for initiating the anionic polymerization of the one or more monomers; and anionically polymerizing the one or more monomers. The polymerization process preferably includes one or more surfactants for forming an emulsion having micelles or a discrete phase including a monomer (e.g., a 1,1-disubstituted alkene compound) distributed throughout a continuous phase (e.g., a continuous phase including a carrier liquid). The surfactant may be an emulsifier, a defoamer, or a wetting agent. The surfactant preferably is present in a sufficient quantity so that a stable emulsion is formed by mixing or otherwise agitating a system including the monomer and carrier liquid. The surfactants according to the teachings herein include one or more surfactants for improving the stability of emulsion (i.e., for improving the stability of the dispersed phase in the carrier liquid phase). The surfactant and/or the amount of surfactant is preferably selected so that all of the monomer micelles are covered by a layer of the surfactant. The surfactant may include an amphoteric surfactant, a nonionic surfactant, or any combination thereof. The surfactant preferably is free of anionic surfactants during the polymerization process. One example of a preferred surfactant (e.g., an emulsifier) is an ethoxylate, such as an ethoxylated diol. For example, the surfactant may include 2,4,7,9-tetramethyl-5-decyne-4,7-diol ethoxylate. The surfactant may include a poly(alkene glycol). Another example of a preferred surfactant is a poly(ethylene glycol)-block-poly(propylene glycol)-block-poly(ethylene glycol) copolymer. Another example of a preferred surfactant is a surfactant including an alcohol, an ethoxylated alcohol, or both. For example, the surfactant may include CARBOWET® 138 nonionic surfactant (including alkyl alcohol, polyethylene glycol, ethoxylated C9-C11 alcohols). Another example of a preferred surfactant is a surfactant including a sorbitan, a sorbitol, or a polyoxyalkene. For example, the surfactant may include sorbitan monopalmitate (nonionic surfactant). Other examples of preferred surfactants include branched polyoxyethylene (12) nonylphynyl ether (IGEPAL® CO-720) and poly(ethylene glycol) sorbitol hexaoleate (PEGSH). The amount of the surfactant (e.g., the amount of the emulsifier) preferably is sufficient to form a layer that substantially encapsulates the monomer and subsequent polymer particles. The amount of surfactant preferably is sufficient so that the discrete phase has a diameter of about 10 mm or less, about 1 mm or less, about 300 µm or less, or about 100 µm or less. The amount of the surfactant is preferably sufficient so that the discrete phase has a diameter of about 0.01 µm or more, about 0.1 µm or more, about 1 µm or more, about 10 µm or more, or about 50 µm or more. The concentration of the surfactant may be about 0.001 weight percent or more, preferably about 0.01 weight percent or more, more preferably about 0.1 weight percent or more, and most preferably about 0.5 weight percent or more, based on the total weight of the emulsion. The concentration of the surfactant may be about 15 weight percent or less, preferably about 10 weight percent or less, and more preferably about 6 weight percent or less, and most preferably about 3 weight percent or less, based on the total weight of the emulsion. The weight ratio of the surfactant to the total weight of the monomer and polymer in the emulsion (e.g., at the end of the polymerization process) preferably is about 0.0001 or more, more preferably about 0.002 or more, even more preferably about 0.005 or more, and most preferably about 0.01 or more. The weight ratio of the surfactant to the total weight of the monomer and polymer in the emulsion (e.g., at the end of the polymerization process) preferably is about 5 or less (i.e., about 5:1 or less), more preferably about 1 or less, even more preferably about 0.5 or less, and most preferably about 0.1 or less. The carrier liquid is preferably water. The polymerization process may include a step of applying shear forces or sonication to a mixture including at least the surfactant and the carrier fluid for forming an emulsion. For example, the process may include stirring or otherwise agitating the mixture for creating the emulsion.

The polymerizable compositions disclosed herein may be polymerized in solution via anionic polymerization processes. In some embodiments the polymerizable compositions may be polymerized utilizing the method disclosed in Palsule et al. U.S. Ser. No. 14/810,741 filed Jul. 28, 2015, incorporated herein in its entirety for all purposes. According to the process disclosed in Palsule et al. the process comprises the steps of mixing one or more 1,1-disubstituted alkenes and a solvent; adding an activator; reacting the activator with the one or more 1,1-disubstituted alkenes to initiate the anionic polymerization of the one or more 1,1-disubstituted alkenes; and anionically polymerizing the one or more 1,1-disubstituted alkenes to form a polymer. The concentration of the monomer in the solution polymerization process may be sufficiently low so that after polymerization, the solution can flow. If the concentration of the monomer is too high, the solution becomes too viscous at the end of the polymerization process and the solution may be difficult to handle. The concentration of the monomer in the solution polymerization process may be sufficiently high so that the polymerization process is economical. The one or more monomers is preferably present at a concentration of about 0.5 weight percent or more, more preferably about 2 weight percent or more, even more preferably about 5 weight percent or more, and most preferably about 8 weight percent or more, based on the total weight of the solvent and monomer. The one or more monomers may be present at a concentration of about 90 weight percent or less, preferably about 75 weight percent or less, more preferably about 50 weight percent or less, even more preferably about 30 weight percent or less, and most preferably about 20 weight percent or less. If the monomer is added at multiple times (such as continuous and/or sequential monomer addition), it will be appreciated that the amount of the one or more monomers refers to the total amount of monomer and polymer and by-products of the monomer that are present when the addition of monomer has been completed. The polymerization process includes one or more solvents selected so that the monomer and solvent form a single phase. Preferably the solvent does not chemically react with the other components of the solution polymerization system during the polymerization process. For example, the solvent preferably does not react with the monomer. As another example, the solvent preferably does not react with the activator. Preferred solvents are organic solvents, or mixtures of organic solvents. Such solvents, or solvent mixtures typically are in a liquid state at the reaction temperature(s) (e.g., during activation and/or during polymerization. The pressure of the solvent (e.g., organic solvent) and of the monomer at the polymerization temperature should be sufficiently low so that the risk of the reactor failing from over-pressure is reduced or eliminated. For example the partial pressure of the solvent, of the monomer, or both, at the polymerization temperature may be about 500 Torr or less, about 200 Torr or less, about 50 Torr or less, or about 5 Torr or less. It may be desirable for the solvent to be substantially or entirely free of any solvent that may react with the monomer via Michael addition. However, by selecting reaction conditions so that the polymerization reaction is sufficiently fast, it may be possible to employ such monomers in the solvent polymerization process. For example, by selecting parameters such as monomer feed rates, reaction temperature, monomer type, and pH, it may be possible to employ a solvent including or consisting of a protic solvent, such as an alcohol. The solution polymerization may be initiated using an activator capable of initiating anionic polymerization of the 1,1-disubstituted alkene containing compound. The solvent and/or one or more of the monomers (e.g., the 1,1-disubstituted alkene compounds) may further contain other components to stabilize the monomer prior to exposure to polymerization conditions or to adjust the properties of the final polymer for the desired use. Prior to the polymerization reaction, one or more inhibitors may be added to reduce or prevent reaction of the monomer. Such inhibitors may be effective in preventing anionic polymerization of the monomer, free radical polymerization of the monomer, reaction between the monomer and other molecules (such as water), or any combination thereof.

The polymerization processes disclosed may include a step of applying shear forces to a mixture including at least the monomer and the solvent or carrier. For example, the process may include stirring or otherwise agitating the mixture for creating the solution or emulsion, for dispersing or removing a precipitated polymer, for controlling thermal gradients, or any combination thereof. The polymerization processes preferably include a reaction temperature at which the partial pressure of the solvent is generally low. For example, the partial pressure of the solvent and/or the monomer may be about 400 Torr or less, about 200 Torr or less, about 100 Torr or less, about 55 Torr or less, or about 10 Torr or less. The reaction temperature preferably is about 80° C. or less, more preferably about 70° C. or less, even more preferably about 60° C. or less, even more preferably about 55° C. or less, even more preferably about 45° C. or less, even more preferably about 40° C. or less, and most preferably about 30° C. or less. The reaction temperature typically is sufficiently high that the solvent or carrier liquid and the monomer are in a liquid state. For example, the reaction temperature may be about −100° C. or more, about −80° C. or more, about −30° C. or more, or about 10° C. or more. When polymerizing a 1,1-disubstituted alkene compound, it may be desirable to add one or more acid compounds to the solution, to the monomer, or both, so that the initial pH of the solution is about 7 or less, about 6.8 or less, about 6.6 or less, or about 6.4 or less. The polymerization process may be stopped prior to the completion of the polymerization reaction or may be continued until the completion of the polymerization reaction. Preferably, the reaction rate is sufficiently high and/or the reaction time is sufficiently long so that the polymerization reaction is substantially complete.

The conversion of the monomer to polymer may be about 30 weight percent or more, about 60 weight percent or more, about 90 weight percent or more, about 95 weight percent or more, or about 99 weight percent or more. The conversion of monomer to polymer may be about 100 weight percent or less.

The polymerizable compositions may further contain other components to stabilize the compositions prior to exposure to polymerization conditions or to adjust the properties of the final polymer for the desired use. For example, in certain embodiments, a suitable plasticizer can be included with a reactive composition. Exemplary plasticizers are those used to modify the rheological properties of adhesive systems including, for example, straight and branched chain alkyl-phthalates such as diisononyl phthalate, dioctyl phthalate, and dibutyl phthalate, trioctyl phosphate, epoxy plasticizers, toluene-sulfamide, chloroparaffins, adipic acid esters, sebacates such as dimethyl sebacate, castor oil, xylene, 1-methyl-2-pyrrolidone and toluene. Commercial plasticizers such as HB-40 partially hydrogenated terpene manufactured by Solutia Inc. (St. Louis, Mo.) can also be suitable.

For example, one or more dyes, pigments, toughening agents, impact modifiers, rheology modifiers, natural or synthetic rubbers, filler agents, reinforcing agents, thickening agents, opacifiers, inhibitors, fluorescence markers, thermal degradation reducers, thermal resistance conferring agents, surfactants, wetting agents, or stabilizers can be included in a polymerizable system. For example, thickening agents and plasticizers such as vinyl chloride terpolymer (comprising vinyl chloride, vinyl acetate, and dicarboxylic acid at various weight percentages) and dimethyl sebacate respectively, can be used to modify the viscosity, elasticity, and robustness of a system. In certain embodiments, such thickening agents and other compounds can be used to increase the viscosity of a polymerizable system from about 1 to 3 cPs to about 30,000 cPs, or more.

According to certain embodiments, stabilizers can be included in the polymerizable compositions to increase and improve the shelf life and to prevent spontaneous polymerization. Generally, one or more anionic polymerization stabilizers and or free-radical stabilizers may be added to the compositions. Anionic polymerization stabilizers are generally electrophilic compounds that scavenge bases and nucleophiles from the composition or growing polymer chain. The use of anionic polymerization stabilizers can terminate additional polymer chain propagation. Exemplary anionic polymerization stabilizers are acids, exemplary acids are carboxylic acids, sulfonic acids, phosphoric acids and the like. Exemplary stabilizers include liquid phase stabilizers (e.g., methanesulfonic acid ("MSA")), and vapor phase stabilizers (e.g., trifluoroacetic acid ("TFA")). Free-radical stabilizers preferably include phenolic compounds (e.g., 4-methoxyphenol or mono methyl ether of hydroquinone ("MeHQ") and butylated hydroxy toluene (BHT)). Stabilizer packages for 1,1-disubstituted alkenes are disclosed in U.S. Pat. Nos. 8,609,885 and 8,884,051, each incorporated by reference. Additional free radical polymerization inhibitors are disclosed in U.S. Pat. No. 6,458,956 and are hereby incorporated by reference. Generally, only minimal quantities of a stabilizer are needed and, in certain embodiments only about 150 parts-per-million or less can be included. In certain embodiments, a blend of multiple stabilizers can be included such as, for example a blend of anionic stabilizers (MSA) and free radical stabilizers (MeHQ). The one or more anionic polymerization stabilizers are present in sufficient amount to prevent premature polymerization. Preferably, the anionic polymerization stabilizers are present in an amount of about 0.1 part per million or greater based on the weight of the composition, more preferably about 1 part per million by weight or greater and most preferably about 5 parts per million by weight or greater. Preferably, the anionic polymerization stabilizers are present in an amount of about 1000 parts per million by weight or less based on the weight of the composition, more preferably about 500 parts per million by weight or less and most preferably about 100 parts per million by weight or less. The one or more free radical stabilizers are present in sufficient amount to prevent premature polymerization. Preferably, the free radical polymerization stabilizers are present in an amount of about 1 parts per million or greater based on the weight of the composition, more preferably about 5 parts per million by weight or greater and most preferably about 10 parts per million by weight or greater. Preferably, the free radical polymerization stabilizers are present in an amount of about 5000 parts per million by weight or less based on the weight of the composition, more preferably about 1000 parts per million by weight or less and most preferably about 500 parts per million by weight or less.

The polymerizable compositions and polymers disclosed herein may be utilized and a number of applications. Exemplary applications include adhesives, sealants, coatings, components for optical fibers, potting and encapsulating materials for electronics, resins and pre-polymers as raw materials in other systems, and the like.

The polymerizable compositions exhibit a number of advantageous properties including rapid reactivity, room or low temperature reactivity, tailorable rheological characteristics, and the like. Polymers prepared from the polymerizable compositions exhibit a number of advantageous properties including for example, high glass transition temperature, high degradation temperature, high heat resistance, high stiffness and modulus, good rigidity and the like.

Other components commonly used in curable compositions may be used in the compositions of this invention. Such materials are well known to those skilled in the art and may include ultraviolet stabilizers and antioxidants and the like. The compositions of the invention may also contain durability stabilizers known in the art. Among preferred durability stabilizers are alkyl substituted phenols, phosphites, sebacates and cinnamates.

Illustrative Embodiments

The following examples are provided to illustrate the invention, but are not intended to limit the scope thereof. All parts and percentages are by weight unless otherwise indicated.

Polymerization Process

A number of polymerizable compositions are polymerized according to the following procedure. Tetrahydrofuran (THF) (9.0 g) and methylene malonate monomers (1.0 g) are charged into a round bottom flask or HDPE bottle. Typically a 10% polymer solution is desired, if 100% conversion of the monomer is to be achieved. Other ratios may be used as desired. A magnetic stirring bar of appropriate size was added into the flask and the mixture is allowed to stir on a magnetic stirring plate for 5 minutes. A 1% solution of tetramethyl guanidine (TMG) in THF, is charged into the flask containing monomer solution under agitation. The amount of activator can represent 1:1000 mole ratio of activator to monomer. Other ratios may be used depending on the speed of reaction desired and molecular weights of the final polymers. The reaction is continued at room temperature for 1 hour. For higher monomer/polymer concentrations (above 10 wt % in solvent) or high molecular weight build-ups, viscosity of the solution visibly increases as molecular weight builds up. Samples are removed for characterization (e.g. GPC) at appropriate time intervals, if molecular weight increase is monitored as an indication of the progress of polymerization. Upon completion of polymerization, a few drops of TFA are added to the solution to quench the reaction. The resulting solution is precipitated into methanol. The precipitate is dried in a vacuum oven at room temperature. The desired polymer is obtained as a white powder.

The polymerization of EBA keto ester monomer is performed in bulk by addition of 1:100 ratio of TMG initiator to monomer in an aluminum pan with no agitation. Polymerization proceeds until the further growth in molecular weight is not possible due to gelation. Polymer is precipitated in methanol and allowed to dry in a vacuum oven without using heat. The subsequent polymer, relatively clean of low molecular weight oligomers and impurities is used for GPC and DSC analysis.

The 1,1-disubstituted alkenes of the polymerizable compositions and the glass transition temperature of the polymers prepared by the disclosed process are shown in Table 1. Glass transition temperatures are determined by DSC plots using a Differential Scanning calorimeter, Q2000 by TA Instruments using a 10° C./minute heating rate. Decomposition profiles were obtained using a Thermogravimetric Analyzer (TGA), Model Q 50 by TA Instruments using a 10° C./minute heating rate.

TABLE 1

| 1,1-disubstituted alkenes | Glass transition temperatures ° C. |
|---|---|
| Fenchyl methyl methylene malonate (F3M), 100% | 151-190 |
| Fenchyl ethyl methylene malonate (FEMM), 100% | 150-175 |
| Menthyl ethyl methylene malonate (MEMM), 100% | 135-145 |
| Phenyl propyl ethyl methylene malonate (PEMM), 100% | 61 |
| Phenyl propyl methyl methylene malonate, (P3M), 100% | 65 |
| Dicyclohexyl methylene malonate (DCHMM), 100% | 140 |
| Ethyl 2-benzoylacrylate (EBA keto ester) | 99 |
| 75% F3M + 25% DEMM | 137 |
| 50% F3M + 50% DEMM | 95 |
| 25% F3M + 75% DEMM | 58 |

Figure 2:
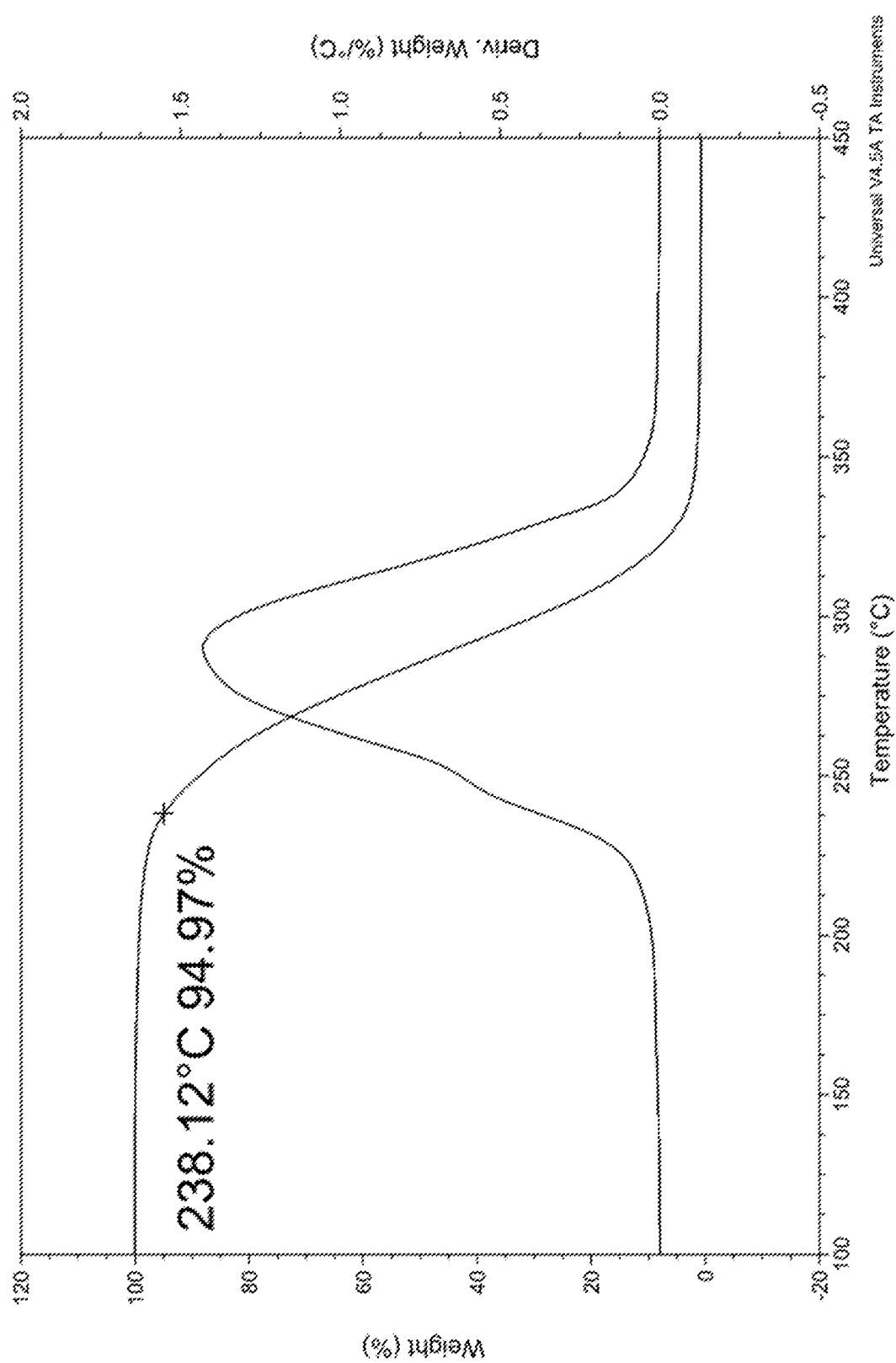
FIG. 2 is a TGA trace of fenchyl ethyl methylene malonate.
Figure 3:
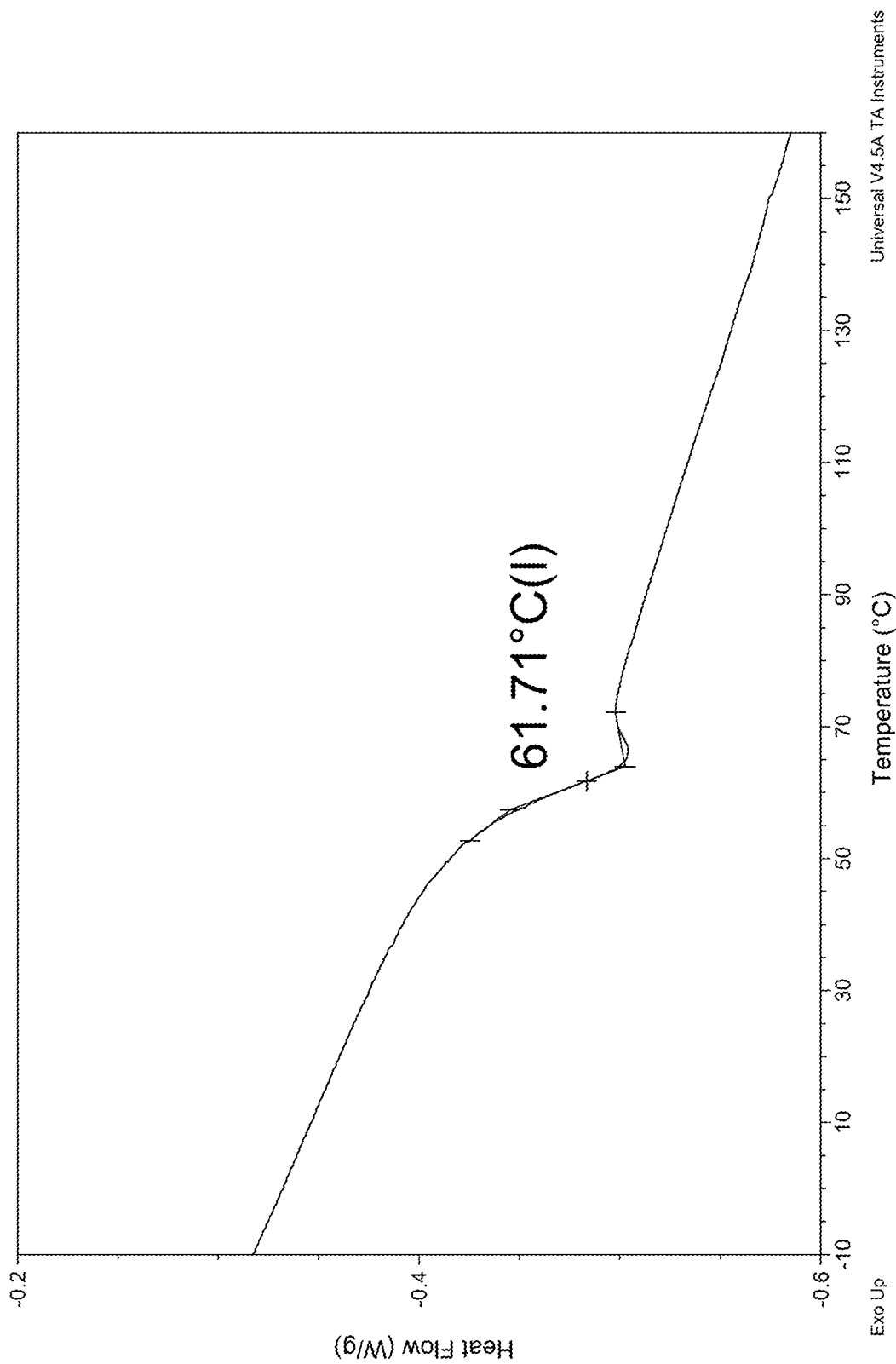
FIG. 3 is a DSC trace of the polymer based on phenyl propyl ethyl methylene malonate (PEMM).
Figure 4:
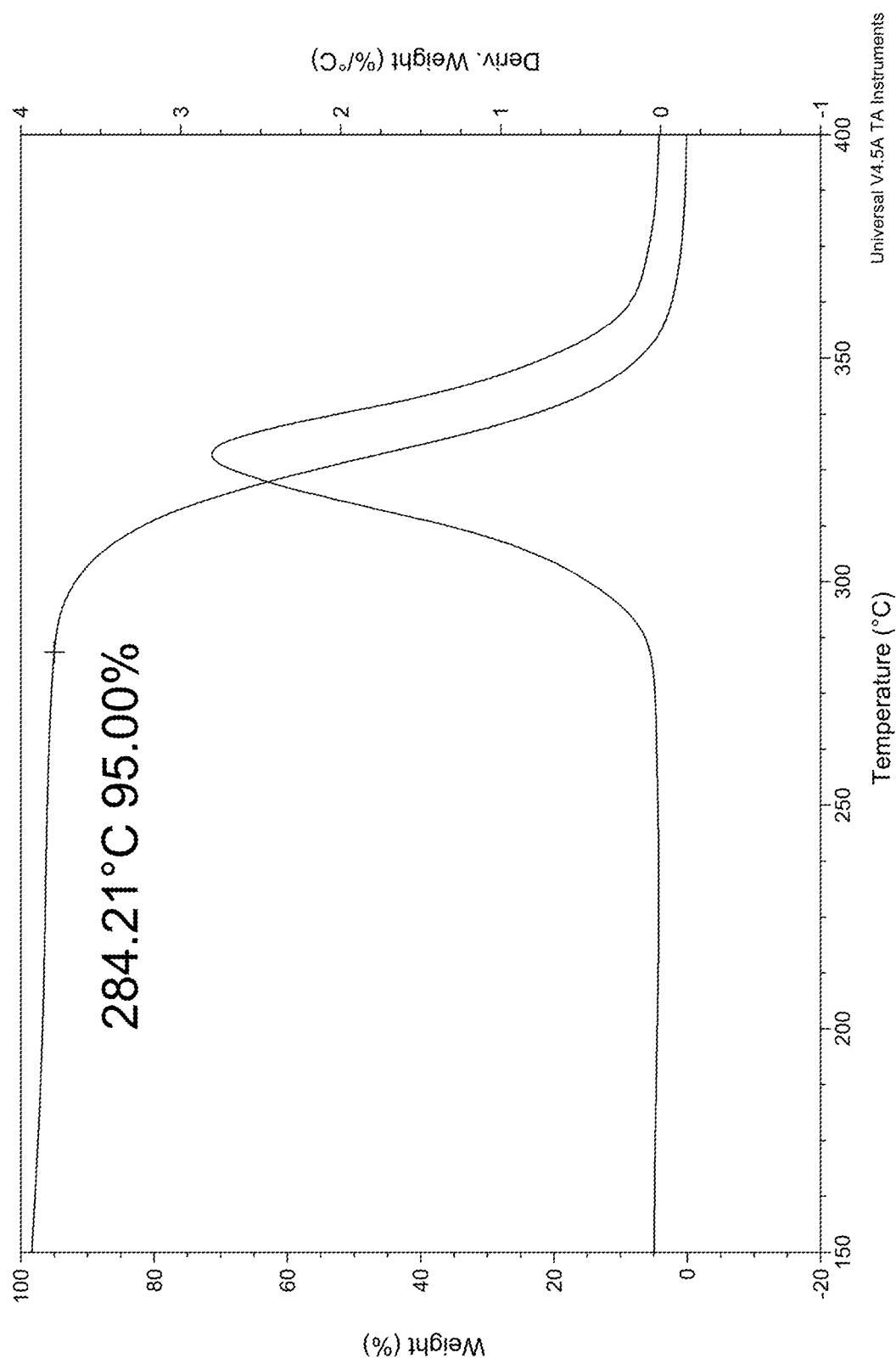
FIG. 4 is a TGA trace of the polymer based on phenyl propyl ethyl methylene malonate (PEMM).
Figure 5:
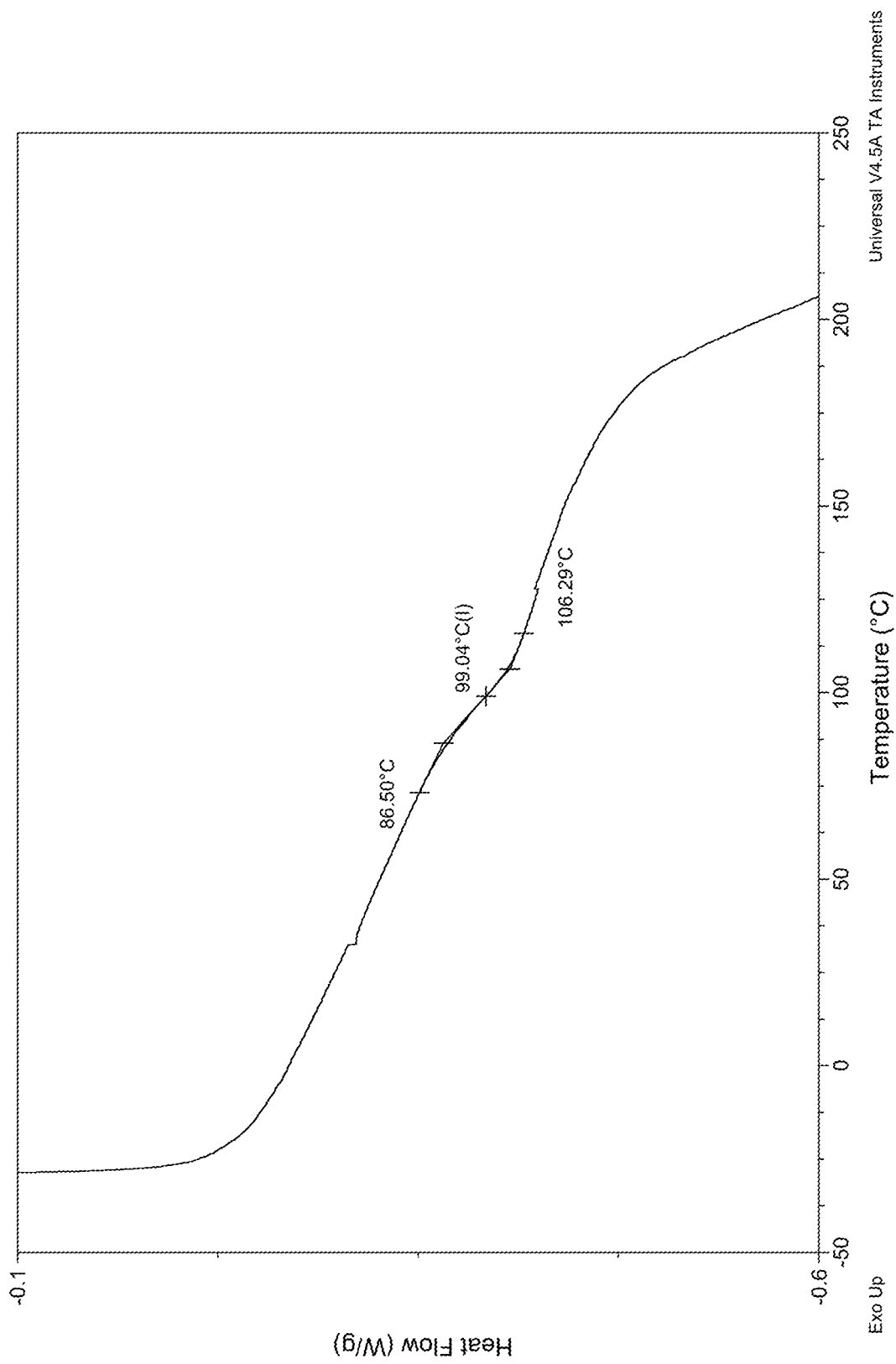
FIG. 5 is a DSC trace of the polymer based on ethyl 2-benzoylacrylate (EBA ketoester).

FIG. 1 is a DSC trace of the polymer based on fenchyl ethyl methylene malonate (FEMM) which shows the glass transition temperature as 175° C. FIG. 2 is a TGA trace of FEMM which shows a decomposition temperature of 238° C. for 95% weight loss. The number average molecular weight of this polymer is 293K and weight average molecular weight is 888K. FIG. 3 is a DSC trace of phenyl propyl ethyl methylene malonate (PEMM) which shows a Tg of 62° C. FIG. 4 is a TGA trace of PEMM which shows a decomposition temperature of 284° C. for 95% weight loss. The number average molecular weight of this polymer is 74.5K and weight average molecular weight is 450K.

The polymer made from EBA keto ester monomer exhibits a number average molecular weight of 14,000 and weight average molecular weight of 32,000K. DSC trace of this polymer shows a Tg of 99° C.

Figure 6:
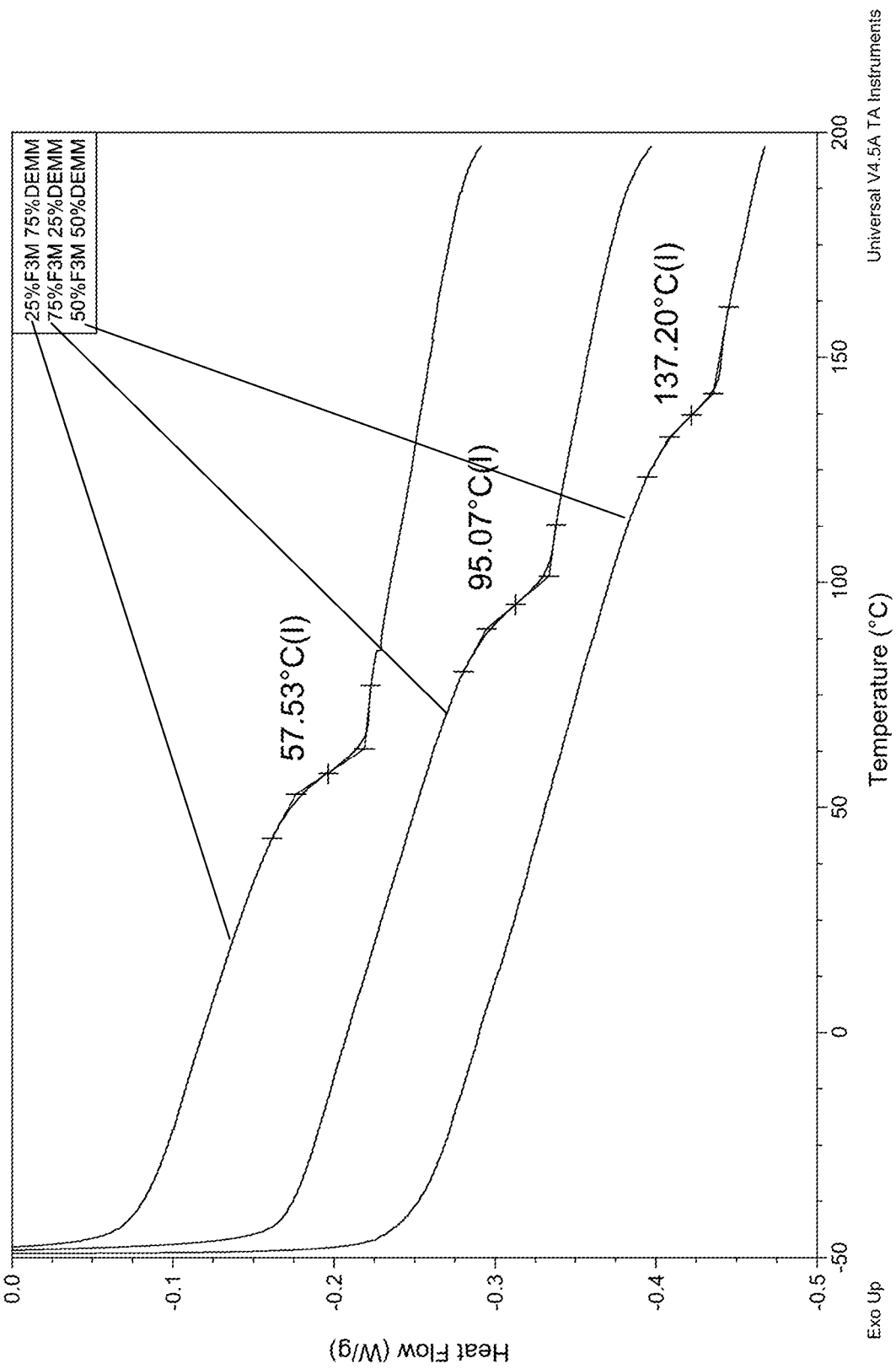
FIG. 6 is a DSC trace of the copolymers of DEMM and F3M in various ratios demonstrating that the Tg can be adjusted by varying the ratios of monomers.

Random copolymers of DEMM and F3M are prepared varying the amount of DEMM and F3M in the feed. FIG. 6 shows the Tg's of 3 random copolymers with varying amounts of DEMM and F3M in the feed. The Tg of the copolymer shifts towards the Tg of the homopolymer depending on which polymer is present in excess in the feed. For a 50:50 ratio of the two monomers in the feed, the Tg of the copolymer is roughly in the middle of the range of the two homopolymer Tgs.

The improvement in mechanical properties of the compositions with the addition of the monomer promoting the formation of polymers with high Tg is confirmed by conducting tensile shear testing. On cold rolled steel panels, an initiator solution of 0.1 wt % sodium pyruvate in ethanol. After the solvent is flashed off the surface of the panel is primed for anionic polymerization. 100% DEMM, 100% FEMM, 50:50 DEMM+FEMM and 75:25 FEMM+DEMM monomers are then applied to the pre-initiated steel surfaces allowing them to polymerize anionically forming an adhesive joint. The surfaces are allowed to cure for 72 hours at room temperature. The results of the tensile shear bond strength after complete cure can be summarized in Table 2 below.

| 1,1 disubstituted alkene monomer of blends | Tensile shear strength (MPa) |
|---|---|
| DEMM | 4.8 |
| FEMM | 5.9 |
| 50% DEMM and 50% FEMM | 10.3 |
| 25% DEMM and 75% FEMM | 14.4 |

The tensile shear strength obtained by blending or copolymerizing the two monomers is much higher than the tensile shear strength obtained with the two homopolymers alone.

These results illustrate that incorporation of groups such as fenchyl, menthyl, 2-phenyl propyl, dicyclohexyl etc. enhance the glass transition temperatures (Tg) of the polymer composition in comparison to diethyl methylene malonate (Tg=30° C.) or dimethyl methylene malonate (Tg=55° C.). Also performance synergies can be obtained by copolymerizing a monomer capable of producing a high Tg polymer with low Tg monomers such as DEMM resulting in improved mechanical properties.

Parts by weight as used herein refers to 100 parts by weight of the composition specifically referred to. Any numerical values recited in the above application include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value, and the highest value enumerated are to be considered to be expressly stated in this application in a similar manner. Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

What is claimed is:

1. A composition comprising one or more 1,1-dicarbonyl-substituted alkene compounds wherein each carbonyl group independently has a hydrocarbyl group bonded to the carbonyl groups by a direct bond, a heteroatom, and the hydrocarbyl groups are selected such that homopolymers prepared from the 1,1-di-carbonyl-substituted alkenes exhibit glass transition temperatures of less than 60° C., and one or more multifunctional 1,1-dicarbonyl-substituted alkene compounds which comprise a core unit of two or more 1,1-dicarbonyl-substituted alkenes which correspond to the formula:

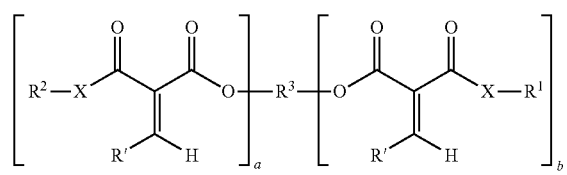

wherein:
R$^1$ is separately in each occurrence a hydrocarbyl group comprising an aryl group, aralkyl group, alkaryl group with the aryl group bonded to the 1 or 2 carbon atom, a cycloalkyl group, an alkyl group with a cycloalkyl group on the 1 or 2 carbon atom, or a branched alkyl group wherein the 1 carbon atom is a tertiary or the 1 and 2 carbon atoms are secondary;
R$^2$ is, separately in each occurrence, alkyl with a primary 1 carbon atom or a secondary 1 carbon atom and a primary second carbon atom, alkenyl with a primary 1 carbon atom or a secondary 1 carbon atom and a primary second carbon atom, alkaryl wherein the aryl group is bonded to a carbon atom which is 3 or more carbon atoms from X, alkyl group with a cycloalkyl group bonded to a carbon atom which is 3 or more carbon atoms from the X, a polyalkylene or ether;
R$^3$ is separately in each occurrence a polyvalent hydrocarbon group;
R' is separately in each occurrence hydrocarbyl or hydrogen;
X is a heteroatom or a direct bond;
a is separately in each occurrence an integer of 1 or more;
b is separately in each occurrence an integer of 0 or more wherein the sum of a and b is 2 or greater and the number of valences of R$^3$ is equal to the sum of a and b;
wherein the one or more 1,1-dicarbonyl-substituted alkene compounds exhibit a purity of 95 mole percent or greater, have one mole percent or less of the analogous 1,1-di-substituted alkane, 1 mole percent or less of an impurity containing a dioxane group, about 1 mole percent of less of any impurity having the alkene group replaced by an analogous hydroxyalkyl group wherein mole percent is based on the total moles in the 1,1-dicarbonyl-substituted alkene compound; and the one or more multifunctional 1,1-dicarbonyl-substituted alkene compounds are present in an amount of about 1 weight percent to less than 100 weight percent.

2. A composition according to claim 1 wherein the 1,1-dicarbonyl-substituted alkenes have hydrocarbyl groups of alkyl with a primary 1 carbon atom or a secondary 1 carbon atom and primary 2 carbon atom, alkenyl with a primary 1 carbon atom or a secondary 1 carbon atom and primary 2 carbon atom, alkaryl wherein the aryl group is bonded to a carbon atom which is 3 or more carbon atoms from the direct bond, oxygen atom, nitrogen atom or sulfur atom, alkyl group with a cycloalkyl group bonded to a carbon atom which is 3 or more carbon atoms from the direct bond, oxygen atom, nitrogen atom or sulfur atom, or a polyalkylene ether.

3. A composition according to claim 1 wherein the one or more 1,1-di-carbonyl-substituted alkenes correspond to formula 3

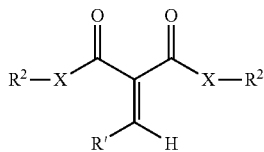

wherein: $R^2$ is, separately in each occurrence a hydrocarbyl group selected such that homopolymers prepared having the selected hydrocarbyl groups exhibit glass transition temperatures of less than 60° C.; R' is separately in each occurrence hydrocarbyl or hydrogen and X is a heteroatom or a direct bond.

4. A composition according to claim 3 wherein $R^2$ is separately in each occurrence alkyl with a primary 1 carbon atom or a secondary 1 carbon atom and primary 2 carbon atom, alkenyl with a primary 1 carbon atom or a secondary 1 carbon atom and primary 2 carbon atom, alkaryl wherein the aryl group is bonded to a carbon atom which is 3 or more carbon atoms from X, alkyl group with a cycloalkyl group bonded to a carbon atom which is 3 or more carbon atoms from the X, or a polyalkylene ether.

5. A composition according to claim 1 wherein the one or more multifunctional 1,1-dicarbonyl-substituted alkene compounds are present in an amount of about 5 weight percent to about 30 weight percent.

6. A composition according to claim 1 wherein the Tg of polymers prepared therefrom is 60° C. or greater.

7. A composition according to claim 1 wherein the Tg of copolymers prepared therefrom is 80° C. or greater.

8. A composition comprising a copolymer prepared from a composition comprising one or more 1,1-dicarbonyl-substituted alkene compounds wherein each carbonyl group independently has a hydrocarbyl group bonded to the carbonyl groups by a direct bond, a heteroatom, and the hydrocarbyl groups are selected such that homopolymers prepared from the 1,1-di-carbonyl-substituted alkenes exhibit glass transition temperatures of less than 60° C., and one or more multifunctional 1,1-dicarbonyl-substituted alkene compounds which comprise a core unit of two or more 1,1-dicarbonyl-substituted alkenes which correspond to the formula:

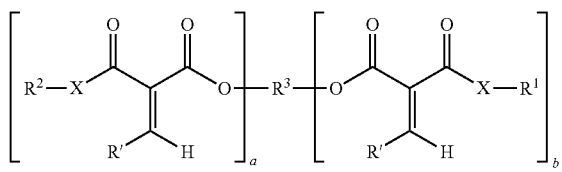

wherein:
$R^1$ is separately in each occurrence a hydrocarbyl group comprising an aryl group, aralkyl group, alkaryl group with the aryl group bonded to the 1 or 2 carbon atom, a cycloalkyl group, an alkyl group with a cycloalkyl group on the 1 or 2 carbon atom, or a branched alkyl group wherein the 1 carbon atom is a tertiary or the 1 and 2 carbon atoms are secondary;

$R^2$ is, separately in each occurrence, alkyl with a primary 1 carbon atom or a secondary 1 carbon atom and a primary second carbon atom, alkenyl with a primary 1 carbon atom or a secondary 1 carbon atom and a primary second carbon atom, alkaryl wherein the aryl group is bonded to a carbon atom which is 3 or more carbon atoms from X, alkyl group with a cycloalkyl group bonded to a carbon atom which is 3 or more carbon atoms from the X, a polyalkylene or ether;

$R^3$ is separately in each occurrence a polyvalent hydrocarbon group;

R' is separately in each occurrence hydrocarbyl or hydrogen;

X is a heteroatom or a direct bond;

a is separately in each occurrence an integer of 1 or more;

b is separately in each occurrence an integer of 0 or more wherein the sum or a and b is 2 or greater and the number of valences of $R^3$ is equal to the sum of a and b;

wherein the one or more multifunctional 1,1-dicarbonyl-substituted alkene compounds are present in sufficient amount to increase the glass transition temperatures of polymers prepared from the composition.

9. A composition according to claim 8 having a glass transition temperature of 60° C. or greater.

10. A composition according to claim 9 wherein the 1,1-dicarbonyl-substituted alkenes have hydrocarbyl groups of alkyl with a primary 1 carbon atom or a secondary 1 carbon atom and primary 2 carbon atom, alkenyl with a primary 1 carbon atom or a secondary 1 carbon atom and primary 2 carbon atom, alkaryl wherein the aryl group is bonded to a carbon atom which is 3 or more carbon atoms from the direct bond, oxygen atom, nitrogen atom or sulfur atom, alkyl group with a cycloalkyl group bonded to a carbon atom which is 3 or more carbon atoms from the direct bond, oxygen atom, nitrogen atom or sulfur atom, or a polyalkylene ether.

11. A composition according to claim 9 wherein the one or more 1,1-di-carbonyl-substituted alkenes correspond to formula 3

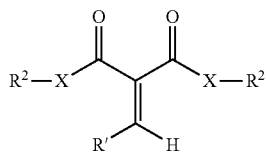

wherein: $R^2$ is, separately in each occurrence a hydrocarbyl group selected such that homopolymers prepared having the selected hydrocarbyl groups exhibit glass transition temperatures of less than 60° C.; R' is separately in each occurrence hydrocarbyl or hydrogen and X is a heteroatom or a direct bond.

12. A composition according to claim 11 wherein $R^2$ is separately in each occurrence alkyl with a primary 1 carbon atom or a secondary 1 carbon atom and primary 2 carbon atom, alkenyl with a primary 1 carbon atom or a secondary 1 carbon atom and primary 2 carbon atom, alkaryl wherein the aryl group is bonded to a carbon atom which is 3 or more carbon atoms from X, alkyl group with a cycloalkyl group bonded to a carbon atom which is 3 or more carbon atoms from the X, or a polyalkylene ether.

13. A composition according to claim 9 wherein the one or more 1,1-dicarbonyl-substituted alkene compounds exhibit a purity of 95 mole percent or greater, have one mole percent or less of the analogous 1,1-di-substituted alkane, 1 mole percent or less of an impurity containing a dioxane group, about 1 mole percent of less of any impurity having the alkene group replaced by an analogous hydroxyalkyl group wherein mole percent is based on the total moles in the 1,1-dicarbonyl- substituted alkene compound.

14. A composition according to claim 9 wherein the one or more multifunctional 1,1-dicarbonyl-substituted alkene compounds are present in an amount of about 1 weight percent to less than 100 weight percent.

15. A composition according to claim 9 wherein the one or more multifunctional 1,1-dicarbonyl-substituted alkene compounds are present in an amount of about 5 weight percent to about 30 weight percent.

16. A composition according to claim 9 wherein the copolymers exhibit a weight average molecular weight of about 2000 to about 3,000,000 daltons and a polydispersity of about 1.01 to 10 as determined Gel Permeation Chromatography.

17. A method comprising contacting one or more of the 1,1-dicarbonyl-substituted alkene compounds with one or more of the multifunctional 1,1-dicarbonyl-substituted alkene compounds according to claim 1 with a polymerization initiator under conditions to polymerize the composition and the glass transition temperature of the resulting polymer is increased over the glass transition temperature of a homopolymer of the one or more 1,1-di-carbonyl-substituted alkene compounds.

18. A method according to claim 17 wherein the one or more multifunctional 1,1-dicarbonyl-substituted alkene compounds are present in an amount of about 1 weight percent to less than 100 weight percent.

* * * * *